(12) United States Patent
Ross et al.

(10) Patent No.: US 10,662,447 B2
(45) Date of Patent: May 26, 2020

(54) SYSTEM AND PROCESS FOR OBTAINING PRODUCTS FROM BIOMASS

(71) Applicant: EE-TERRABON BIOFUELS, LLC, New Braunfels, TX (US)

(72) Inventors: Michael Kyle Ross, Bryan, TX (US); Cesar B. Granda, College Station, TX (US)

(*) Notice: Subject to any disclaimer, the term of this patent is extended or adjusted under 35 U.S.C. 154(b) by 0 days.

(21) Appl. No.: 14/135,044

(22) Filed: Dec. 19, 2013

(65) Prior Publication Data
US 2014/0178951 A1 Jun. 26, 2014

Related U.S. Application Data

(60) Provisional application No. 61/755,270, filed on Jan. 22, 2013, provisional application No. 61/745,392, filed on Dec. 21, 2012.

(51) Int. Cl.
*C07C 51/48* (2006.01)
*C12P 7/40* (2006.01)
*C12P 39/00* (2006.01)
*C12P 7/64* (2006.01)
*B01D 11/04* (2006.01)

(52) U.S. Cl.
CPC ........ *C12P 7/6409* (2013.01); *B01D 11/0426* (2013.01); *C07C 51/48* (2013.01); *C12P 7/40* (2013.01); *C12P 39/00* (2013.01)

(58) Field of Classification Search
None
See application file for complete search history.

(56) References Cited

U.S. PATENT DOCUMENTS

| | | | | |
|---|---|---|---|---|
| 5,962,307 | A | * | 10/1999 | Holtzapple ............ C12M 21/04 435/290.4 |
| 6,087,532 | A | * | 7/2000 | Baniel ..................... C12P 7/56 562/580 |
| 7,790,012 | B2 | | 9/2010 | Kirk et al. |
| 7,875,163 | B2 | | 1/2011 | Gilliam et al. |
| 7,993,500 | B2 | | 8/2011 | Gilliam et al. |
| 7,993,511 | B2 | | 8/2011 | Gilliam et al. |
| 8,232,440 | B2 | | 7/2012 | Holtzapple et al. |
| 8,362,306 | B2 | | 1/2013 | Wheeler et al. |
| 8,431,368 | B2 | | 4/2013 | Hamelers et al. |
| 2010/0203625 | A1 | | 8/2010 | Holtzapple et al. |
| 2011/0042230 | A1 | | 2/2011 | Gilliam et al. |
| 2011/0079515 | A1 | | 4/2011 | Gilliam et al. |
| 2011/0083968 | A1 | | 4/2011 | Gilliam et al. |
| 2011/0111475 | A1 | * | 5/2011 | Kuhry ..................... C12N 1/22 435/166 |
| 2011/0147227 | A1 | | 6/2011 | Gilliam et al. |

FOREIGN PATENT DOCUMENTS

WO 2010074469 A2 7/2010
WO 2010082772 A2 7/2010

OTHER PUBLICATIONS

Huang et al., Journal of Membrane Science, vol. 288, pp. 1-12 (2007).*
Huang et al., Journal of Membrane Science, vol. 288, pp. 1-12; 2007 (of record).*
Ke-Ke Cheng et al.. Downstream Processing of Biotechnological Produced Succinic Acid. Appl Microbiol Biotechnol. Jun. 16, 2012, 95(4), 841-850.
Search Report and Written Opinion dated Mar. 28, 2014 for International Application No. PCT/US2013/076589 (10 pgs.).

* cited by examiner

*Primary Examiner* — Soren Harward
*Assistant Examiner* — Paul D. Pyla

(57) ABSTRACT

A process for producing products from biomass comprising fermenting biomass to produce a first product stream comprising carboxylic acid salts; acidifying at least one of the first product stream and a second product stream to produce a third product stream comprising acids; extracting such acids from the third product stream with a solvent; separating the extracting solvent from the acids to produce the separated extracting solvent and a fourth product stream comprising acids; and processing the fourth product stream to produce a fifth product stream.

13 Claims, 13 Drawing Sheets

SYSTEM AND PROCESS FOR OBTAINING PRODUCTS FROM BIOMASS

CROSS-REFERENCE TO RELATED APPLICATIONS

This application claims the benefit under 35 U.S.C. § 119(e) of U.S. Provisional Patent application Nos. 61/745,392 filed Dec. 21, 2012, and 61/755,270 filed Jan. 22, 2013, the disclosures of which are hereby incorporated herein by reference.

STATEMENT REGARDING FEDERALLY SPONSORED RESEARCH OR DEVELOPMENT

Not applicable.

BACKGROUND

Technical Field

This disclosure pertains to a method for converting organic salts produced in buffered mixed-acid fermentation into acids, followed by extraction to recover the acids from an aqueous solution. Embodiments of the disclosure also pertain to integrating such aspects with the conversion of the acids to products, such as ketones and acetates.

Background

Typical conversion of organic salts to acid requires the addition of acid or the regeneration of resins using acids, which results in a large waste stream of salts and inability to regenerate the base to be used in the fermentation. This is costly and not environmentally friendly.

Terminology and Glossary

Throughout this specification, the following terminology applies:

"VFAs"—Abbreviation for "volatile fatty acids", which are the organic acids of carboxylic type produced in anaerobic fermentation by naturally occurring consortia of anaerobic bacteria. Namely these VFAs are short- and medium-chain fatty acids such as acetic, propionic, butyric, iso-butyric, valeric, iso-valeric, caproic, enanthic, caprylic, pelargonic acids, and combinations thereof. Smaller amount of higher acids, such as decanoic and undecanoic have also been detected in analyses. These acids are neutralized in the fermentation to control pH thus ending up with the salts of the acids also known as VFA salts. The terms VFA (or VFAs in plural), short- and medium-chain fatty acids, carboxylic acids, or organic acids may be used interchangeably.

"EAU"—Electrochemical Acidification Unit. Generic term that refers to any unit that employs techniques for electrochemically acidifying a solution.

"LMW Ketones"—Low-molecular-weight—used to denote ketones that are preferably, but not limited to C4 and C5 ketones.

"HMW Ketones"—High-molecular-weight—used to denote ketones that are preferably, but not limited to, C8 and C9 ketones.

"CED"—Abbreviation for "conventional electrodialysis"

"EDI"—Abbreviation for "electrodionization"

"EDBM"—Abbreviation for "Electrodialysis with bi-polar membranes".

"OLAL"—Organic liquid-Aqueous liquid

"GOLAL"—Gas-Organic liquid-Aqueous liquid

"MCFA"—Medium-chain fatty acid

"Biomass"—Any biological material.

In addition to what is typically done to acidify fermentation broth, which is adding acids, which produces waste streams and has high operating expenditures, some processes also use the so called "acid springing process". This entails contacting a carboxylate solution (e.g., ammonium) with a solvent, such as trioctylamine (TOA) or TOPO (Trioctylphosphine oxide) with the fermentation broth (made out of calcium or ammonium salts of the organic acids). Carbon dioxide could be added or the ammonia could be removed by evaporation. The resulting complex of TOA or TOPO would then be heated to decompose and release the acid.

Several problems exist with such processes, including the fact that the end product is seldom only calcium or only ammonium salts; instead, there is routinely a mixture of salts that may contain problematic components or impurities, such calcium, ammonium, sodium, potassium, magnesium, iron, etc. When there is a mixture of these cations, the process described above cannot be applied efficiently or effectively. In addition, the solvents used are very expensive, so losses are of serious concern.

Organic acids are the most common metabolites produced in fermentations. Most microorganisms produce organic acids in preference to other types of compounds such as alcohols. Such is the case because there is a thermodynamic advantage to producing organic acids as their energy state is lower than most other metabolites such as alcohols. This thermodynamic advantage makes their production a more robust process. It is, therefore, advantageous to allow microorganisms to produce organic acids.

In addition, as biochemicals, organic acids are valuable compounds. Citric acid, succinic acid, ascorbic acid, pyruvic acid, gluconic acid, lactic acid, formic acid, acetic acid, propionic acid, butyric acid, valeric acid, caproic acid are some examples of valuable organic acids that can be produced by fermentation. However, recovery of such acids from the fermentation broth, especially those that are soluble in water, has been over the years considered a challenge.

Organic acids generally have a higher boiling point than water, which makes it difficult to separate them by distillation; therefore, typically extraction is the preferred method. However, acids tend to lower pH of the fermentation, which in general inhibits microorganism growth. In addition, most acids are toxic to microorganisms in their unionized state. As a result, a buffering agent (e.g., sodium hydroxide) is added to control pH. Such neutralization of the acids generates the salts of the acid, which due to their ionic state are difficult to recover by extraction.

Because the acid must be in its non-ionic state to be efficiently extracted, processes that produce organic acids typically must either operate the fermentation at a low pH, which is not always possible due to inhibitions, or they must add acids, such as sulfuric acid, to the resulting fermentation effluent. Although some salts of the mineral acid, such as sulfate salts, maybe decomposed back into the mineral acid (e.g., sulfate salts decompose into sulfur dioxide, $SO_2$, which may be used as an acid itself or it may be converted into sulfur trioxide, $SO_3$, which may be dissolved in water to recovery sulfuric acid), such conversion occurs at very high temperatures, so it may be costly; therefore, generally the addition of acid generates a waste stream of salts, such as sodium sulfate, which is undesirable as they constitute an environmental hazard and a significant operational cost for disposal.

Electrochemical Techniques

The best known electrochemical process for acidification is known as electrodialysis, particularly using bi-polar membranes (EDBM). Electrodialysis (ED) was discovered in 1890, with most of its breakthrough developments occurring in the 1930's, 1940's and 1950's. Since then, research, uses and industrial implementation of ED have increase exponentially.

FIGS. 1A-1C shows conventional 3- (FIG. 1A) and 2-chamber (FIGS. 1B-1C) EDBMs. The basic set up of an ED system makes use of a direct current supply, electrodes 100A and 100B, perm-selective ion-exchange membranes 101A & 101B, solvents 103, and electrolytes 104. The basic principle of its operation is that direct current is applied to electrodes 100A and 100B to allow the positive (cations 105) or negative (anions 106) electrolytes in the solvent to be transported towards the opposite charged electrode (100A for the cations and 100B for the anions), while the ion-exchange membranes 101A and 101B allow passage or retain the electrolytes 104 and thus achieve the desired effect. As mentioned, among the electrochemical acidification techniques, Electrodialysis with Bi-polar Membranes (EDBM) is probably the best known method, which make use of bi-polar membranes 102 (membranes with positive and negative charges) to split water and generate acid (hydrogen/hydronium ions) or base (hydroxide ions).

Other electrochemical techniques produce the hydrogen/hydronium ions at the electrode. A good example of these techniques was developed by Gilliam et al. with focus on the production of alkaline solutions. Such system, dubbed as Alkalinity Based on Low Energy (ABLE) is disclosed in U.S. Pat. Nos. 7,993,511, 7,993,500, 7,875,163, 7,790,012, U.S. patent application Ser. No. 12/989,781, U.S. patent application Ser. No. 13/021,355, U.S. patent application Ser. No. 12/952,665 and U.S. patent application Ser. No. 12/991,898 incorporated by reference in their entirety for all purposes. The ABLE technique oxidizes hydrogen at the anode to hydrogen/hydronium ions and produces hydroxide ions at the cathode. The acidic and basic solutions are separated by perm-selective membranes. Two variations of this technique have been devised and their description follows:

The first technique consumes electricity and produces hydrogen gas at the cathode, while releasing hydroxide ions into the solution in which the cathode is submerged. The hydrogen produced may be directed to the anode to be oxidized, which releases the hydrogen ions into the solution in which the anode is submerged thus acidifying it.

In the second technique, which is very similar to how a fuel cell operates, oxygen is supplied to the cathode so that it is reduced to produce hydroxide ions, which are released into the solution in which the cathode is submerged. At the anode, on the other hand, extraneous hydrogen gas is introduced and oxidized to produce hydrogen ions, which are released into the solution in which the anode is submerged. In this technique, electricity may be generated and exported rather than consumed.

In both of Gilliam's techniques appropriate and suitable catalysts may be applied in the anode and cathode to improve the efficiency of the reaction. Also in both of Gilliam's techniques, to make the reaction more favorable, carbon dioxide may be introduced into the solution in which the cathode is submerged to lower the pH and form carbonate and bicarbonate ions as the hydroxide ions are released.

Ion-Exchange Background

Ion exchange is a well established technique for recovery, purification, separation and decontamination of aqueous and other ion-containing solutions using a polymeric or mineral 'ion exchanging' media. Such media in its fresh or regenerated state carries a certain type of ion, be it a cation with positive charge or an anion with negative charge and it releases these cations or anions, while at the same time uptakes cations or anions, respectively from the ion-containing solution, thus causing 'ion exchange'. The media will keep exchanging ions until it is exhausted of the original ion. At that point, the media needs to be regenerated by passing through a concentrated solution containing the original ion it held. Because of this regeneration step, typically, to allow uninterrupted continuous operation, two or more ion exchange beds are operated, so that one or more beds may operate, while others are being regenerated.

Known ion exchangers of the mineral type are zeolites and clay. However, more efficient systems employ polymeric resins, such as, but not limited to, those manufactured by Dow Water Solutions (Dowex™ and Amberlite™ resins). Within the group of polymeric resins, there are anion exchange resins and cation exchange resins.

One consideration in regard to use of ion exchange as compared to electrochemical techniques is that the capital cost is lower. However, another consideration is that the typical operation mode for ion exchange is that once the ion exchange bed needs to be regenerated, an acid, such as sulfuric or hydrochloric acid, has to be used thus generating a waste stream of inorganic salts that must be dealt with. Also, in addition to the operating costs for the acid and regeneration waste disposal, the base employed as buffering agent for pH control in the fermentation is not recovered and must be replenished, which adds even more to the operating costs. Such waste issues and non-recoverability of the buffering agent for the fermentation raises not only economic, but also environmental concerns, which have made researchers consider electrochemical techniques over ion exchange as the more feasible, economical and environmentally friendly option.

To ensure that a process using cation exchange may be both economically and environmentally sustainable, a different method for regenerating the cation exchange media is necessary. For such purpose, many have proposed the regeneration of the media using high-pressure carbon dioxide and water. Such regeneration produces the bicarbonate ($HCO_3^-$) salt of the cation absorbed (e.g, $Na^+$, $K^+$). Pressures that have been used for this process range from as low as about 15 psi to over 3600 psi. The CARIX process, for instance, is a well established process that has been used for water demineralization, which uses high-pressure $CO_2$ for regeneration. After regeneration, when the pressure is released, a lot of the $CO_2$ is released; therefore, $CO_2$ recycle is sometimes implemented.

Liquid-Liquid Extraction Under High-Pressure Carbon Dioxide

Several researchers have proposed the recovery of carboxylic acids from their salts using high-pressure $CO_2$ for acidification, while using liquid-liquid extraction to remove the acids from the aqueous phase. Pressures as high as 50 bars were tested, but no improvement was typically observed above 30 to 40 bars. Baniel et al. patented a process for extraction of lactic acid using amines as the extracting solvent under high pressure $CO_2$.

The discussion above establishes that there is the need for effective and cost-efficient processes that are able to convert the organic salts into the non-ionized organic acid to allow efficient and cost-effective extraction without the production of undesirable streams (e.g., salt waste streams).

SUMMARY

Herein disclosed is a process for producing products from biomass comprising: fermenting biomass to produce a first product stream comprising carboxylic acid salts; acidifying at least one of the first product stream, a second product stream, and combinations thereof to produce a third product stream comprising acids; extracting acids from the third product stream with a solvent, and subsequently separating the extracting solvent from the acids to produce the separated extracting solvent and a fourth product stream comprising acids; processing the fourth product stream to produce a fifth product stream; and recycling at least a portion of the fourth product stream or the fifth product stream for use as at least part of the extracting solvent.

In some embodiments, fermenting biomass comprises anaerobic fermentation with a mixed culture of microorganisms in a fermentation vessel or systems of vessels. In some embodiments, the second product stream results from intermediate processing of the first product stream, and wherein the second product stream comprises carboxylic acid salts.

In some embodiments, acidifying comprises using an electrochemical acidification unit (EAU). In some embodiments, prior to extracting acids, the third product stream undergoes at least one of degasifying, deionizing, and concentrating with reverse osmosis. In some embodiments, processing the fourth product stream comprises fractionating the acids. In some embodiments, processing the fourth product stream comprises converting at least a portion of the acids to ketones. In some embodiments, the conversion occurs in a catalytic ketone reactor. In some embodiments, processing the fourth product comprises converting at least a portion of the acids to ethyl acetate.

In some embodiments, wherein acidifying comprises using ion exchange with high pressure CO2 regeneration. In some embodiments, prior to extracting acids, the third product stream undergoes at least one of degasifying, deionizing, and concentrating with reverse osmosis. In some embodiments, wherein processing the fourth product stream comprises fractionating the acids. In some embodiments, wherein processing the fourth product stream comprises converting at least a portion of the acids to ketones. In some embodiments, the conversion occurs in a catalytic ketone reactor. In some embodiments, processing the fourth product comprises converting at least a portion of the acids to ethyl acetate. In some embodiments, the CO2 for regenerating the ion exchange beds is mostly obtained from the CO2 generated in the fermentation.

In some embodiments, acidifying comprises using high pressure CO2 while performing liquid-liquid extraction. In some embodiments, prior to extracting acids, the third product stream undergoes at least one of degasifying, deionizing, and concentrating with reverse osmosis. In some embodiments, processing the fourth product stream comprises fractionating the acids. In some embodiments, processing the fourth product stream comprises converting at least a portion of the acids to ketones. In some embodiments, the conversion occurs in a catalytic ketone reactor. In some embodiments, processing the fourth product comprises converting at least a portion of the acids to ethyl acetate. In some embodiments, the CO2 for the acidification with high-pressure CO2 while performing liquid-liquid extraction is mostly obtained from the CO2 generated in the fermentation. In some embodiments, concentrating with reverse osmosis occurs at a pressure not lower than the acidification with high-pressure CO2 while performing liquid-liquid extraction.

In some embodiments, the carboxylic acid salts further comprise volatile fatty acid (VFA) salts.

In some embodiments, using an EAU results in production of a hydroxide stream, and wherein at least some of the hydroxide stream is recycled for use in the fermenting step. In some embodiments, the regeneration of the ion exchange beds with high-pressure CO2 results in the production of a carbonate or bicarbonate stream, and wherein at least some of the carbonate or bicarbonate stream is recycled for use in the fermenting step.

In some embodiments, the acidification with high-pressure CO2 while performing liquid-liquid extraction results in the production of a carbonate or bicarbonate stream, and wherein at least some of the carbonate or bicarbonate stream is recycled for use in the fermenting step.

In some embodiments, intermediate processing of the first product stream comprises at least one of screening, clarifying, dewatering, purifying, concentrating, softening, degasifying, stripping, and ion exchange. In some embodiments, the EAU is operably configured with electrodialysis with bi-polar membranes (EDBM) with at least 2-stages. In some embodiments, the EAU is operably configured with the ABLE system with at least 2-stages.

Herein also disclosed is a process for producing products from biomass comprising: fermenting biomass to produce a first product stream comprising carboxylic acid salts; producing acids from the first product stream, a second product stream, and combinations thereof, to form a third product stream; extracting acids from the third product stream with a solvent, and separating the extracting solvent from the acids to produce the separated extracting solvent and a fourth product stream comprising acids; processing the fourth product stream to produce a fifth product stream; and recycling at least a portion of the fifth product stream to act as the extracting solvent.

In some embodiments, the second product stream results from intermediate processing of the first product stream, and wherein the second product stream comprises carboxylic acid salts. In some embodiments, intermediate processing of the first product stream comprises at least one of screening, clarifying, dewatering, purifying, concentrating, softening, degasifying, stripping, and ion exchange.

Further disclosed is a process for producing medium-chain fatty acids from biomass comprising: fermenting biomass to produce a first product stream comprising carboxylic acid salts; acidifying at least one of the first product stream, a second product stream, and combinations thereof to produce a third product stream comprising acids; allowing the third product stream to phase separate into an organic and an aqueous phase; and recovering medium-chain fatty acids from the organic phase. In some embodiments, the short-chain fatty acids are VFAs in the C2-C5 range. In some embodiments, the medium-chain fatty acids are VFAs in the C4-C11 range, or in the C4-C8 range.

In some embodiments, fermenting biomass comprises anaerobic fermentation with a mixed culture of microorganisms in a fermentation vessel or system of vessels. In some embodiments, the second product stream results from intermediate processing of the first product stream, and wherein the second product stream comprises carboxylic salts. In some embodiments, acidifying comprises using an electrochemical acidification unit (EAU). In some embodiments, acidifying comprises using ion exchange with high pressure CO2 regeneration. In some embodiments, the CO2 for regenerating the ion exchange beds is mostly obtained from the CO2 generated in the fermentation. In some embodiments, acidifying comprises using high pressure CO2 while performing liquid-liquid extraction. In some embodiments, the $CO_2$ for acidification with high-pressure $CO_2$ while performing liquid-liquid extraction is mostly obtained from the $CO_2$ generated in the fermentation. In some embodiments, the carboxylic acid salts further comprise volatile fatty acid (VFA) salts. In some embodiments, prior to allowing the third product stream to phase separate, the third product stream undergoes at least one of degasifying, deionizing, and concentrating with reverse osmosis.

In some embodiments, using an EAU results in production of a hydroxide stream, and wherein at least some of the hydroxide stream is recycled for use in the fermenting step. In some embodiments, the regeneration of the ion exchange beds with high-pressure CO2 results in the production of a carbonate or bicarbonate stream, and wherein at least some of the carbonate or bicarbonate stream is recycled for use in the fermenting step. In some embodiments, the acidification with high-pressure CO2 while performing liquid-liquid extraction results in the production of a carbonate or bicarbonate stream, and wherein at least some of the carbonate or bicarbonate stream is recycled for use in the fermenting step.

In some embodiments, intermediate processing of the first product stream comprises at least one of screening, clarifying, dewatering, purifying, concentrating, softening, degasifying, stripping, and ion exchange.

In some embodiments, the EAU is operably configured with electrodialysis with bi-polar membranes (EDBM) with at least 2-stages. In some embodiments, the EAU is operably configured with the ABLE system with at least 2-stages.

In some embodiments, concentrating with reverse osmosis occurs at a pressure not lower than the acidification with high-pressure CO2.

In some embodiments, at least a portion of the aqueous phase in the third product is recycled to the fermentation. In some embodiments, the aqueous phase in the third product comprises short-chain fatty acids.

The foregoing has outlined rather broadly the features and technical advantages of the invention in order that the detailed description of the invention that follows may be better understood. Additional features and advantages of the invention will be described that form the subject of the claims of the invention. It should be appreciated by those skilled in the art that the conception and the specific embodiments disclosed may be readily utilized as a basis for modifying or designing other structures to accomplish the same purposes of the invention. It should also be realized by those skilled in the art that such equivalent constructions do not depart from the spirit and scope of the invention as set forth in the appended claims.

BRIEF DESCRIPTION OF THE DRAWINGS

For a more detailed description of the present invention, reference will now be made to the accompanying drawings, wherein.

DETAILED DESCRIPTION

Figure 1:
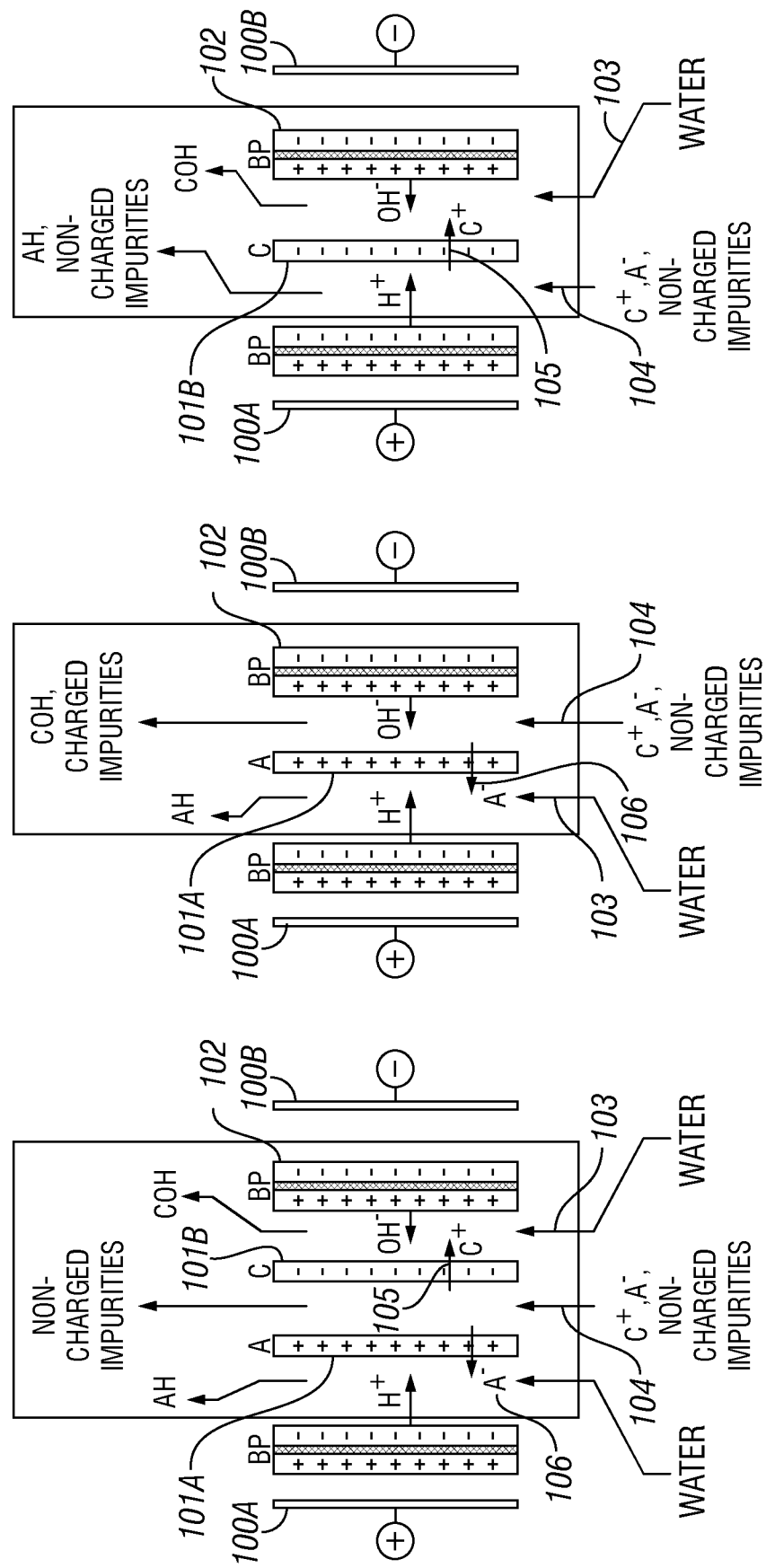
FIG. 1A shows a prior-art three-compartment EDBM configuration for converting salts into acids.
FIGS. 1B and 1C show various prior-art two-compartment EDBM configurations for converting salts into acids.

Herein disclosed are novel apparatuses, systems, and methods that pertain to converting organic salts produced in buffered mixed-acid fermentation into acids.

It should be understood that, although example implementations of embodiments of the disclosure are described herein, the systems, methods, and processes of this disclosure may be implemented using any number of techniques, whether currently known or not. The present disclosure should in no way be limited to the example implementations, drawings, and techniques illustrated below. Additionally, the drawings are not necessarily drawn to scale and may not illustrate obvious pieces of equipment such as valves, certain pumps, vessels, piping, safety equipment, and instrumentation. One of ordinary skill in the art would readily understand the difference between a general process flow diagram (PFD) as compared to the intricate and detailed aspects involved with an actual process. PFD(s) are described in general detail for brevity.

It is also noted, and as would be apparent to one of skill in the art, "process streams" described herein need not be clean cut or pure. When referring to particular product streams herein, it should be understood that, although the primary product(s) may be described, other products may exist in the product stream. Thus, there may be quantities of the other compounds in such streams and/or other impurities.

When referring to particular product streams herein, it should be understood that, although the primary product(s) may be described, other products may exist in the product stream. For example, if as LMW ketones for extraction of the VFAs, the preferred butanone-pentanone (C4-C5) ketones are used, the bulk of the C4-C5 ketone stream might comprise butanone and pentanone, but it may also contain, in addition to some water, small quantities of acetone, other ketones, and/or impurities.

Embodiments of the disclosure are often described in a stepwise manner (e.g., describing process flow step-by-step), but the disclosure should in no manner be limited. That is, one of skill in the art would easily grasp and understand the continuous operation that accommodates embodiments described, discussed, and illustrated. Although flow streams or products are often described as 'sent' from one location to another, the disclosure encompasses use of any and all aspects of fluid/product handling and transport (e.g., pumps, piping, vessels, etc.) that are well within the grasp of a skilled artisan. Finally, although any process stream may be shown as directed to a particular destination (e.g., unit operation, vessel, system, etc.), the destination and handling of the process stream are not limited to such a depiction. Thus, a process stream may be sent to a screen, a clarifier, a reverse osmosis unit, an ion exchange bed, combinations thereof, etc.

Embodiments disclosed herein provide conversion of organic salts into acids, and include and/or integrate one or more of Electrochemical Acidification (EA) processes (e.g., Electrodialysis with bi-polar membranes); Ion exchange with regeneration by high-pressure carbon dioxide; and Liquid-liquid extraction under high-pressure carbon dioxide Electrochemical Acidification Processes Generally, and in accordance with the disclosure, an Electrochemical Acidification Unit (EAU) is any system or unit operation that involves electricity and permselective ion-exchange membranes that results in the production of hydrogen/hydronium ions. Hydrogen/hydronium ions may acidify the solution and allow the acids to be further extracted in a separate extraction system.

In general, any kind of electrochemical process that may use or employ electrodes to achieve the transport of anions or cations as they pass or are retained through ion-exchange membranes may be used.

Integration of Mixed Carboxylic Acids Production with Electrochemical Acidification Processes Mixed carboxylic acids production uses naturally occurring anaerobic bacteria to convert any anaerobically biodegradable material or biomass into the carboxylic acids known as volatile fatty acids (VFAs), such as acetic, propionic, butyric, iso-butyric, valeric, iso-valeric, caproic, enanthic, caprylic, pelargonic acids and mixtures thereof. These acids are neutralized with a buffering agent, such as, but not limited to, sodium or potassium hydroxide, thus producing the organic salts of the acids. These organic salts may be further recovered and chemically converted into valuable chemicals and fuels; however, the recovery and chemistry may be simplified, if the salts are first converted to the acids. Examples of processes that produce mixed carboxylic acids can be found in U.S. patent application Ser. No. 12/629,285 and U.S. patent application Ser. No. 12/745,226, incorporated by reference in entirety for all purposes.

For mixed carboxylic acid production, electrochemical techniques, such as EDBM or the Gilliam's techniques may be used for acidification of salts. The EDBM may be able to efficiently split water into hydrogen and hydroxide ions and the Gilliam's techniques produce hydrogen/hydronium ions from hydrogen in the anode, and hydroxide ions in the cathode. The acids are then recovered by extraction and optionally followed by chemical conversion of the acids into chemicals, such as ethyl acetate, ketones and fuels as described herein.

For converting the salts into the acid form, EDBM configurations may be employed, including a three-compartment configuration (e.g., FIG. 1A), a two-compartment configuration (e.g., FIGS. 1B and 1C), etc. Similarly, Gilliam's techniques can also be operated in several configurations, including two-compartment configuration, three-compartment configuration, four-compartment configuration, etc. In such configurations of an EAU, a solution containing the salts and other impurities, such as a clean/solid free fermentation broth, may be fed thereto, while water or other solution is provided to the other compartments to allow the carrying out of the species that cross the membranes.

By way of a non-limiting example, in a three-compartment configuration, both the cations and anions cross the membranes and end up in their corresponding streams leaving behind only non-charged or weakly charged impurities. In this configuration, both the base and acid produced are purified and have a concentration that is dependent on the amount of water being fed into those compartments.

As another example, a two-compartment configuration, on the other hand, may be set up by having an anion exchange membrane or cation exchange membrane. The difference between the configuration with the anion exchange membrane and the configuration with the cation exchange membrane is that in the former two-compartment example the anion (e.g., the organic anion) may go through the membrane and may be substituted by $OH^-$ in the original solution, which may result in a more purified acid solution with a concentration that depends on the rate of water being fed to the compartment, whereas the base stays with non-charged or weakly charged impurities. On the other hand, in the latter two-compartment example, it is the cation (e.g., sodium or potassium) that may go through the membrane, thus ending up with a purer base and with the acid remaining with the non-charged or weakly charged impurities.

The particular technique used may depend on the original concentration of the organic anion as it exits the fermentation step or unit 203 and may also depend on the size of the organic anions for which recovery is sought. For example, where a three-compartment EAU might be desired because it both purifies the resulting acids and bases, as well as concentrates them, such configuration becomes expensive as the size of the organic anion increases. In such case, a combination of conventional ED or other concentration technique and a two-compartment EAU may give better results in terms of performance and cost.

Similarly to the specific example with EDBM, the particular mode of operation as to when to use the EAU 202 (single unit or system), which may include a two- or three-compartment configuration, depends on many factors, such as specific impurities present, environmental concerns, capital costs and operation and maintenance costs, and so forth.

Figure 2:
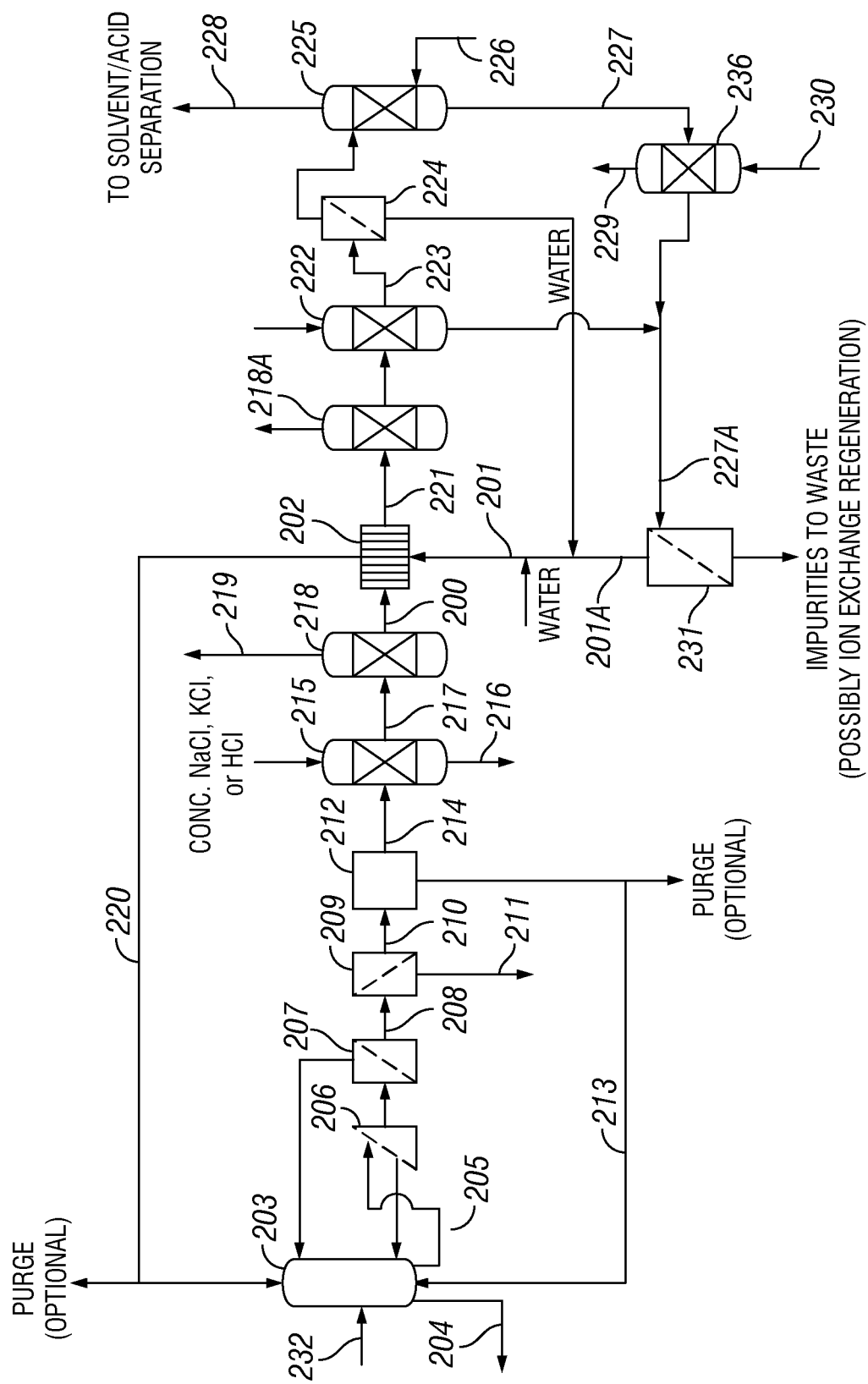
FIG. 2 shows a process diagram that includes use of a fermentation system where biomass to be fermented into carboxylic acids salts or volatile fatty acid (VFAs) salts is fed thereto and the salts are converted to acids using an EAU, according to embodiments of the disclosure.
Figure 3:
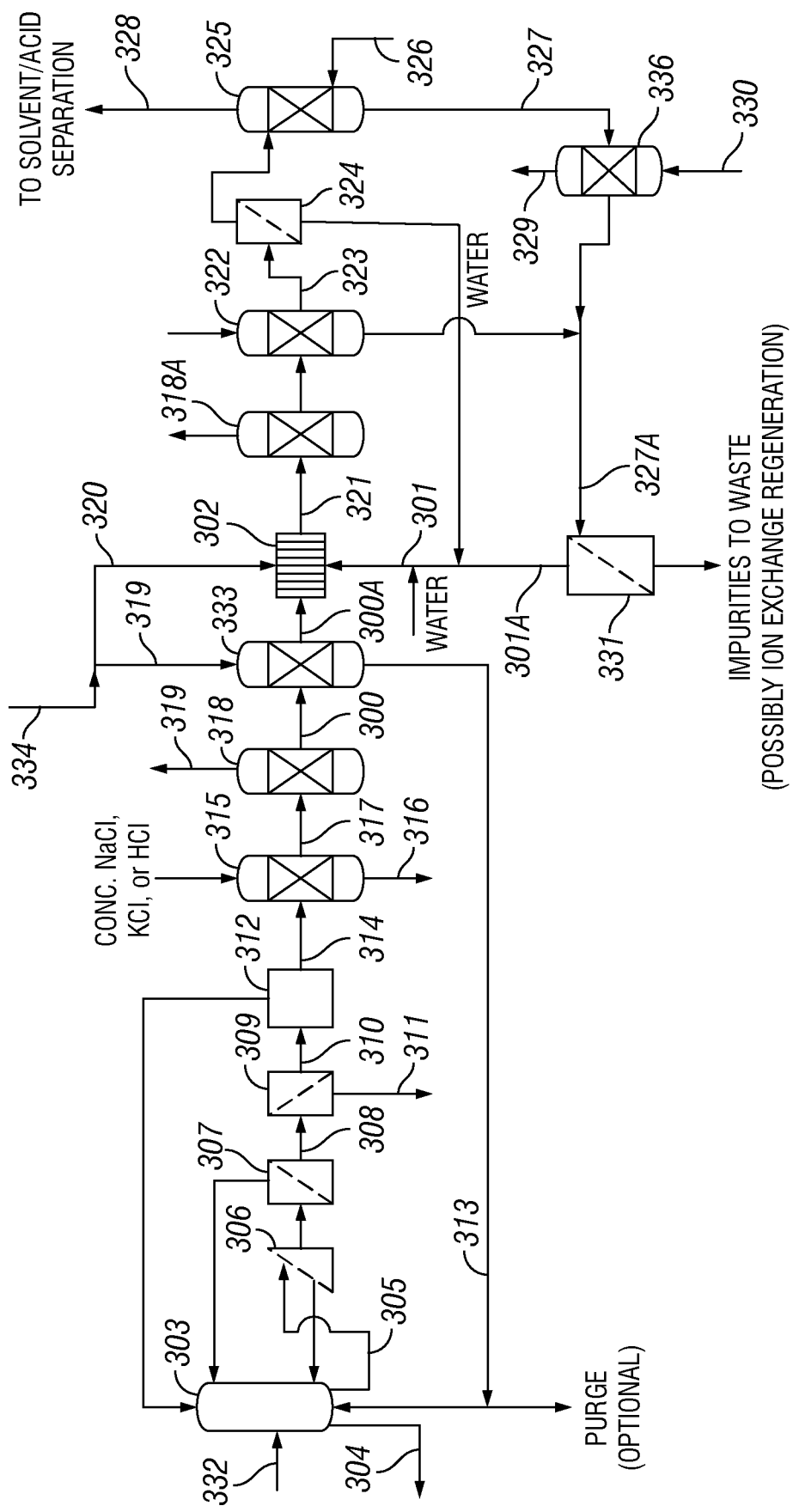
FIG. 3 shows a process comparable to that of FIG. 2, where an anion exchange step is added to concentrate and purify VFA salts and convert salts into a single cation salt prior to entering an EAU system, according to embodiments of the disclosure.
Figure 4:
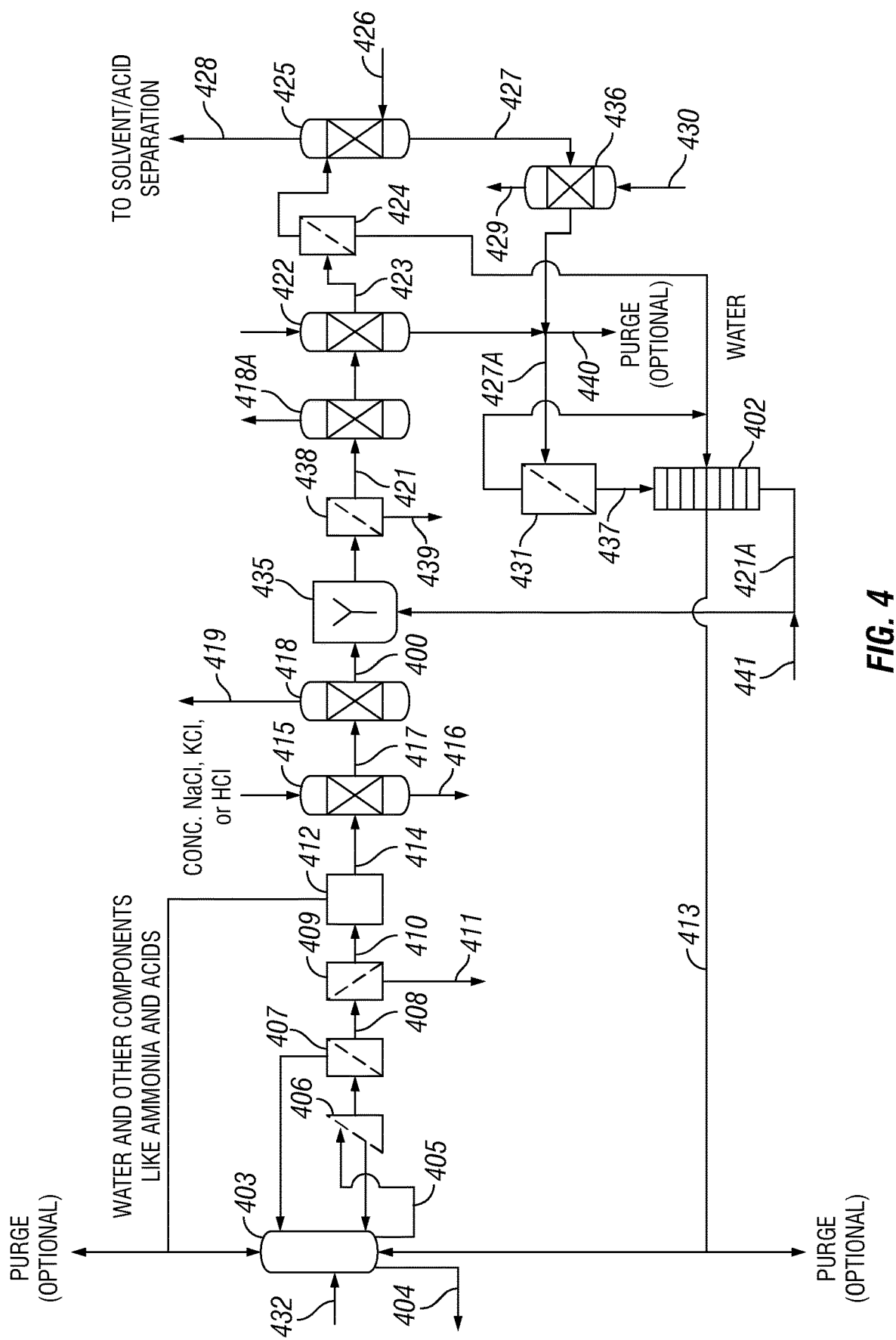
FIG. 4 shows a process comparable to that of FIG. 2, where the VFA salts are acidified by a strong mineral acid and such mineral acid is then regenerated using an EAU system, according to embodiments of the disclosure.

FIGS. 2 through 5, which will now be described, illustrate various processes that may be used or integrated with embodiments disclosed herein. FIGS. 2 through 5 may include the use of an EAU 202, 302, 402, 502. FIGS. 2 through 4 may be more suited towards two-compartment EAUs in the specifics for the integration of mixed carboxylic acid production; however, such suitability is not meant to infer that other EAU configurations cannot be used therewith. In an analogous manner, FIG. 5 may be more suitable for a three-compartment EAU configuration because of the ability to purify both the acid and the bases, and yield a neutral solution with non-charged impurities.

Now with particular reference to FIG. 2, a process diagram for biomass to be fermented into carboxylic acids or volatile fatty acids (VFAs), in accordance with embodiments disclosed herein, is shown. Such fermentation system 203 may be any vessel or system of vessels of different configurations such as, but not limited to, those described in U.S. patent application Ser. No. 12/708,298, incorporated by reference in its entirety for all purposes, and other peripheral devices such as, but not limited to, grinders, pumps, heat exchangers for keeping the adequate temperature in the fermentation, and liquid/solid separators such as, but not limited to, screw-presses, belt presses, plate-and-frame presses, screens and centrifuges. Microorganisms convert the biomass into VFAs, which get neutralized with a buffering agent (e.g., sodium carbonate), thus producing VFA salts. Some of the biomass may remain unreacted and may be removed from the system 203 as undigested residue or digestate 204.

The fermentation broth 205 that exits the fermentation, which may contain the VFA salts, may be sent optionally through a screen 206 to remove large solids and then sent to clarification (or clarifier) 207 to produce a clean (e.g., clarified, solids/free, etc.) effluent 208. The clarification process may be, but is not limited to, micro- or ultra-filtration membranes, flocculation, coagulation, dissolved-air flotation, electrocoagulation, combinations thereof, and so forth. The cleaner effluent 208 from clarification may optionally go through further cleaning 209 with tighter membranes (e.g., in the nanofiltration range) to clean proteins and other impurities, thus generating a concentrate stream 211, which may be exported as a by-product or it may be recycled to the fermentation (not shown).

The clean permeate 210 (or any fermentation product stream) containing the VFA salts may then undergo dewatering or concentration 212. Such concentration may be done using methods such as, but not limited to, reverse osmosis (RO), evaporation, conventional electrodialysis (CED), electrodionization (EDI) or combinations thereof. Water (with other compounds possibly) 213 removed during dewatering or concentration 212 may be recycled back to fermentation 203 or undergo further cleaning for outfall. The concentrate product 214 may be sent to a softener ion exchange bed (or the like) 215 where impurities 216, including multi-valent cations such as magnesium, calcium, iron and others, which tend to form insoluble salts, may be removed if necessary.

The softener bed 215 may be regenerated with sodium or potassium chloride or hydrochloric acid producing a stream of these multi-valent cations chlorides (e.g., calcium, magnesium, iron chloride). This step may keep these ions from fouling the membranes in the EAU system 202. The impurity or ion (e.g., multi-valent-cation) free stream 217 may then optionally pass through a degasifier (e.g., stripper, etc.) 218 to remove gases 219, such as dissolved carbon dioxide. It may be desired to regenerate the softener ion exchange bed with hydrochloric acid to cause a drop in pH that allows carbon dioxide to be removed more easily; however, it is within the scope of the disclosure that degassing may occur prior to softening step.

After gases such as carbon dioxide are removed, the solution stream 200 may be sent to the EAU 202 where VFA salts may be converted into acids. The base stream 220 generated in this step may be recycled to the fermentation 203 for pH control, although, some of this base may be purged, which may help avoid accumulation of cations and/or other impurities. The water 201 used in the EAU 202 may come from any available sources, such as, but not limited to, from the dewatering or concentration step 212, or from any RO cleaned water 201A from upstream. The EAU product stream with acids 221 may be optionally sent to a degasifier (e.g., stripper, etc.) 218A to remove gas(es), such as carbon dioxide. For any unconverted salts, ion exchange unit 222 may be used to convert these VFA salts to acids. Operation of unit 222 may include the use of hydrochloric or sulfuric acid for regeneration. The acid stream 221 or 223 may be further concentrated with RO 224 prior to being sent to acid extraction 225, where the appropriate solvent 226 may be used to remove the acids, resulting in an acid-lean raffinate stream 227. Solvent and acids may be extracted via line 228 and sent to a solvent/acid separation system (not shown).

The acid extraction step or unit 225 may include a number of configurations, including the embodiment shown in FIG. 2. After acids are extracted by the extracting solvent 226, the acid-lean raffinate 227 exiting the extraction, which may contain some dissolved salts and impurities, may also contain a considerable quantity of the extracting solvent 226; therefore, a technique, such as, but not limited to, stripping/ stripper 236 (particularly if the extracting solvent is more volatile than water) may be used. Steam 230 may be introduced to stripper 236. Stream 229 from the stripper 236, which may contain recovered solvent 226, may be sent to a solvent/acid separation system (not shown in FIG. 2). The acid-lean raffinate 227, 227A may be concentrated with RO 231 to recover clean water 201A, which may be used in the EAU system 202. The raffinate stream 227, 227A may ultimately be sent to waste treatment for disposal.

FIG. 3 shows a process like that as shown in FIG. 2, except for the addition of anion exchange step/process 333. Anion exchange step or unit 333 may be used to concentrate and purify the VFA salts (be it from fermentation or any intermediate process step or unit operation therebetween) and to convert the salts into a single cation salt (e.g., ammonium salt) prior to entering the EAU system 302. An anion exchange 333 may extract negatively charged ions (i.e., anions) from the solution 300. Such ions may include the VFA salts. This step may be used in addition to or instead of the dewatering step(s) shown in FIG. 2, FIG. 3, etc.

From the anion exchange step 333, buffer 313 may be obtained and recycled to the fermentation 303, except for some of this stream 313 that may be optionally purged. On the other hand, the base 320 generated in the EAU system 303, which may be substantially a single cation (e.g., ammonium hydroxide in FIG. 3), may be used to regenerate the anion exchange unit or bed 333. Some make-up 334 of the single cation (e.g., ammonia or ammonium hydroxide in FIG. 3) may be added as needed. It may be possible and optional that the cation exiting the EAU 302 be concentrated prior to being used as the regenerant in the anion exchange system 333.

FIG. 4 shows a process like that as shown in FIGS. 2 and/or 3, and illustrates an embodiment where VFA salts may be acidified by an acid, such as a strong mineral acid, in an acidification unit 435. Such acid may be, but is not limited to, hydrochloric acid, sulfuric acid, nitric acid, mixtures thereof, etc. This embodiment may be useful where acidification causes precipitation of certain impurities found in impurity stream 439, which may then be removed prior to extraction. The acidified broth 421 may continue, as comparably described herein (e.g., for FIGS. 2-3, etc.), and including optionally through a $CO_2$ degasifier step 418A and/or an ion-exchange polisher 422. These unit operations may be made optional because of the ability to add acid directly to the broth 405, 408, 410, 414, 417, 400, etc. in the acidification unit 435.

The acidified broth 421, 423 may also be concentrated with RO 424 and then sent to extraction step or unit 425. In the extraction 425, organic acids may be removed, while cations from the VFA salts, and the anions from the mineral acids, may be left behind in the raffinate 427. The raffinate 427 may optionally undergo stripping (e.g., steam stripping) 436 to remove any volatile extracting solvent into overheads 429. A purge 440 may be performed after stripping 436 to avoid accumulation of impurities and salts within the system, which may be sent to waste treatment. The mineral salts in the raffinate stream(s) 427, 427A may undergo concentration in RO 431, and then may be sent to the EAU 402. In the EAU 402, mineral salts may be converted back into mineral acids 421A to be recycled to the acidification step 435. Any make-up of acid 441 may be added into the process as applicable and/or necessary.

Figure 5:
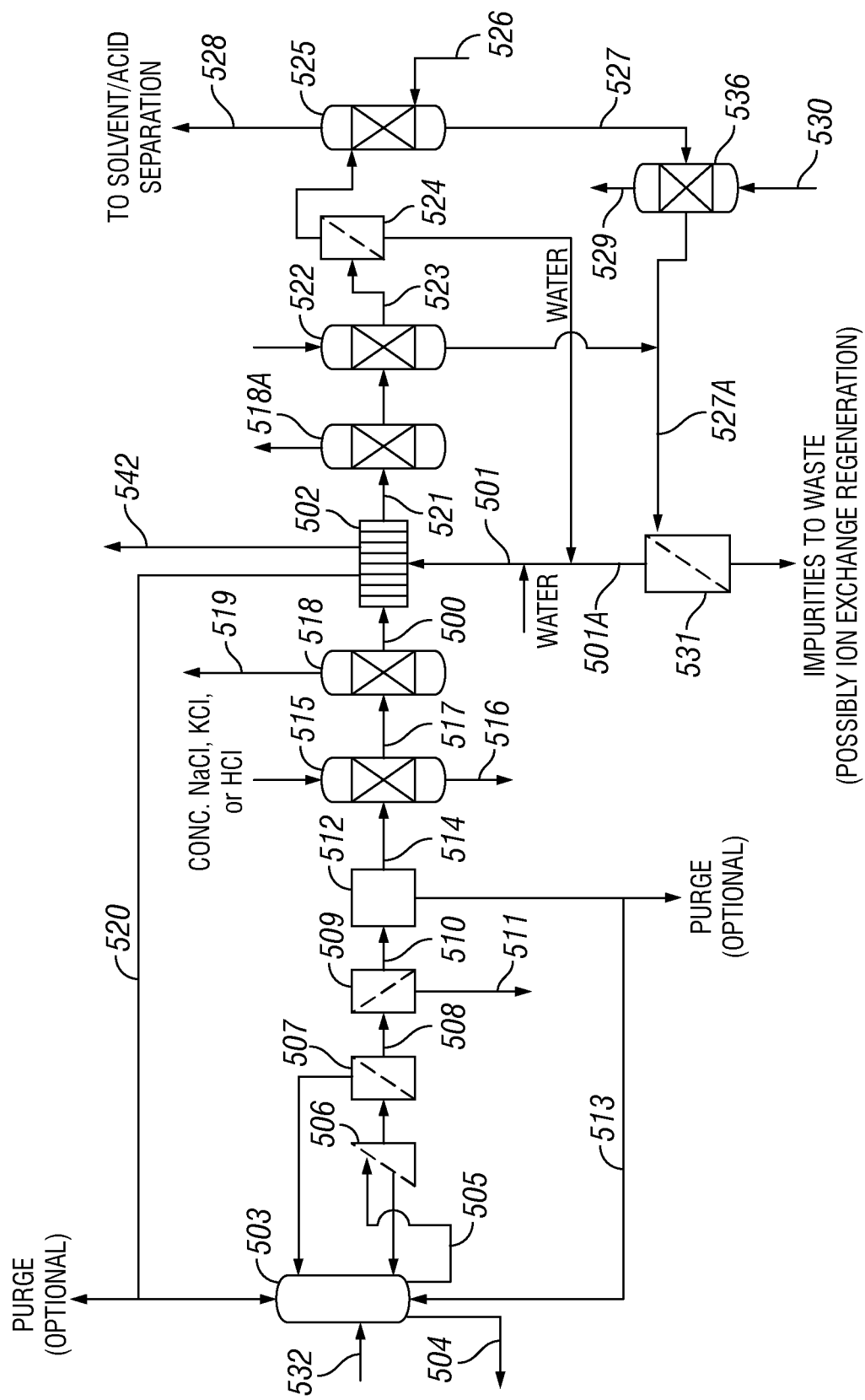
FIG. 5 shows a process comparable to that of FIG. 2, where a 3-compartment EAU is employed, according to embodiments of the disclosure.

Referring now to FIG. 5, which shows a process comparable to those of FIGS. 2-4, except that a 3-compartment EAU 502 is employed. The use of such system may yield purer base 520 and acid 521 streams with all the neutral impurities kept in the middle compartment. Such impurities 542 may then purged from the system, and may then be sent to waste treatment, or may be in some aspects recycled to the fermentation step/unit(s).

When medium-chain fatty acids, such as, but not limited to, caproic, enanthic, caprylic, pelargonic acid, combinations thereof (e.g., acids larger than C6, C6-C9), etc. are present in sufficiently high concentrations, and after the acidification as described herein and illustrated by embodiments of FIGS. 2 through 5 is performed, these acids may phase out of solution. The acids may be selectively separated by a simple liquid-liquid separation step, while other fatty acids, such as short-chain fatty acids (e.g., acetic, propionic, butyric, pentanoic, combinations thereof, etc.), may remain in the aqueous phase, such that extraction may continue as described herein.

If medium-chain fatty acids are the product and it is desired for the shorter-chain fatty acids to undergo elongation as proposed by some researchers, the short-chain fatty acids may still be present in the aqueous phase, are not extracted but recycled to the fermentation so that they may continue the elongation process. As such, liquid-liquid extraction system is not needed, or would be considered as optional. In FIGS. 2-5, similar reference numerals denote similar parts/apparatuses with similar functions and should be thus understood.

Integration of Carboxylic Acid Production with Ion Exchange with High-Pressure $CO_2$ Regeneration.

Figure 6:
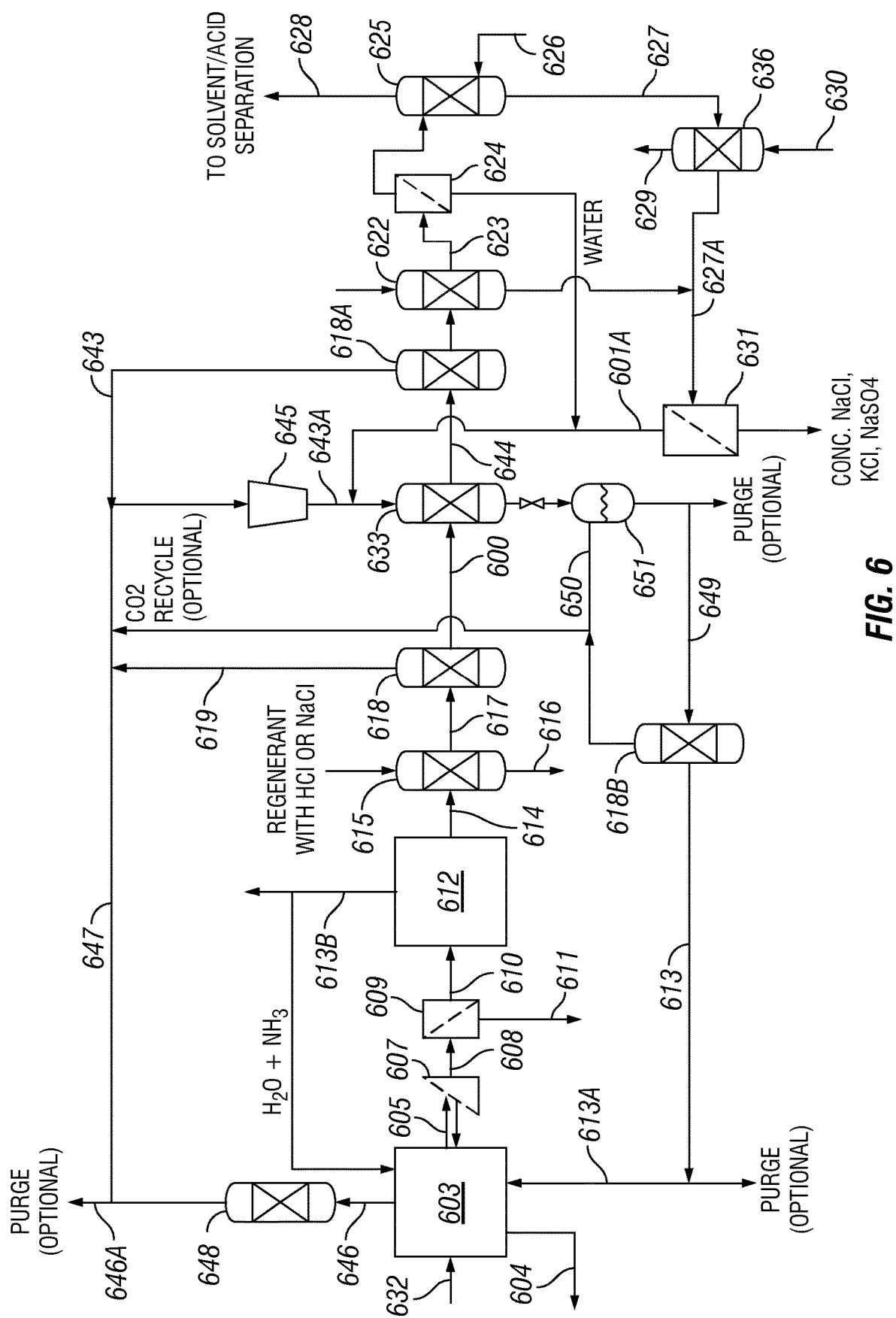
FIG. 6 shows a process that includes integration of carboxylic acid (VFA) salts production in anaerobic fermentation and conversion of the VFA salts to acids using ion exchange with high-pressure $CO_2$ for regeneration, according to embodiments of the disclosure.

FIG. 6 shows the integration of the production of carboxylic acid (volatile fatty acids—VFA) salts in an anaerobic fermentation process with ion exchange with high-pressure $CO_2$ regeneration for recovery of organic acids produced. The biomass 632 to be fermented into VFAs (or fermentation broth) 605 is fed to a fermentation system 603. Such fermentation system 603 may include any vessel or system of vessels of different configurations such as, but not limited to, those described in U.S. patent application Ser. No. 12/708,298, incorporated herein in its entirety for all purposes, and other peripheral devices such as, but not limited to, grinders, pumps, heat exchangers for keeping the adequate temperature in the fermentation, and liquid/solid separators such as, but not limited to, screw-presses, belt presses, plate-and-frame presses, screens and centrifuges.

Microorganisms convert the biomass 632 into VFAs, which may be neutralized with a buffer or buffering agent 613A (e.g., sodium carbonate), resulting in production of VFA salts. Some of the biomass 632 may remain unreacted and be removed from the system 603 as undigested residue or digestate 604. The fermentation broth 605 that exits the fermentation 603, which contains VFA salts, may be sent through a screen (not shown) to remove large solids and/or sent to clarification 607, which may result in a clean (e.g., solids/free, clarified, etc.) effluent 608. The clarification process 607 may be, but is not limited to, micro- or ultra-filtration membranes, flocculation, coagulation, dissolved-air flotation, electrocoagulation, and/or combinations thereof. The cleaner effluent 608 (or broth 605) may go through membrane cleaning (e.g., nanofiltration) 609, which may clean/remove proteins and other impurities, thus generating a concentrate stream 611, which may be exported as a by-product or it may be recycled to the fermentation (not shown in figure).

The clean permeate 610 (or broth 605, etc.) containing the VFA salts may undergo dewatering or concentration 612. Concentration step 612 may be accomplished by, for example, reverse osmosis (RO), evaporation, electrodialysis (CED), electrodionization (EDI), combinations thereof, and so forth. The water (possibly with other compounds) 613B that may be removed during dewatering or concentration 612 may be recycled back to fermentation 603 or undergo further cleaning for outfall. The concentrate 614 may be sent to a softener ion exchange bed 615 where multi-valent cations such as magnesium, calcium, iron, and others, which tend to form insoluble salts, may be removed if necessary or as desired.

The softener bed 615 may be regenerated with sodium or potassium chloride or hydrochloric acid, producing a stream of these multi-valent cations chlorides (e.g., calcium, magnesium, iron chloride) 616. This step may be used to keep these ions from fouling the ion-exchange media as they precipitate. The multi-valent-cation free stream 617 may be optionally passed through a degasifier (e.g., stripper, etc.) 618 to remove gases 619, including, for example, dissolved carbon dioxide. In this regard, it might be better to regenerate the softener ion exchange bed with hydrochloric acid to cause a drop in pH, which may allow carbon dioxide to be removed more easily. In embodiments, degassing 618 may occur prior to softening 615.

After gases 619 are removed, the product stream 600 may be sent to a main ion exchange bed 633, where monovalent cations, such as, but not limited to, sodium, potassium and ammonium, may be replaced by hydrogen ions, which may result in an acidified fermentation broth 644. The acidified broth 644 with the acids may be sent to a degasifier (e.g., stripper, etc.) 618A, which may be used to remove gases, such as carbon dioxide. In the event of any unconverted salts, ion exchange unit 622 may be used to fully convert the VFA salts to acids. Unit 622 may use hydrochloric or sulfuric acid for regeneration. The clean acid stream 623 may be further concentrated with RO 624 prior to acid extraction 625. In acid extraction 625, an appropriate solvent 626 may be used to remove the acids. Solvent and acids may be extracted via line 628 and sent to a solvent/acid separation system (not shown).

The acid extraction 625 may have many configurations, including the embodiment illustrated by in FIG. 6. After the acids are extracted by the extracting solvent 626, the acid-lean raffinate 627 exiting the extraction 625, which may contain some dissolved salts and impurities, may also contain a considerable quantity of the extracting solvent 626. Thus, a process or operation, such as, but not limited to, stripping 636 (such as when the extracting solvent is more volatile than water), may be used. The stream 629 from the stripper operation 636, which may contain recovered solvent, may be sent to a solvent/acid separation system (not shown). The stripped, acid-lean raffinate 627A may be concentrated with RO 631, such as to recover clean water. Resultant clean water 601A may be used (or combined with the high-pressure $CO_2$ 643A) for regeneration of the ion exchange resin of bed 633. The raffinate stream may ultimately be sent to waste treatment for disposal.

In embodiments, two or more ion exchange beds may used so that while one or more are operating, the other or others may be regenerated. This type of operation, or swinging, allows for continuous operation. Regeneration may be done by pressurizing $CO_2$ (e.g., 647, 643) with a pressurization device 645, such as, but not limited to, a gas compressor. $CO_2$, including in substantial quantities, may come from the fermentation process 603, where the buffer 613A, which may be mostly carbonates, may release the $CO_2$ as neutralization of the acids produced takes place to control pH.

Also, some of the $CO_2$ 646 may be produced from the biology of the fermentation 603. In this sense, this excess $CO_2$ may need to be purged 646A and sent to an odor control system (e.g., a biofilter, etc.). Prior to being sent to the pressurization device 645, $CO_2$ 646 may be passed through a scrubber 648 or series of scrubbers to remove certain impurities such as, but not limited to, volatile acids and hydrogen sulfide.

In addition to or alternative of the scrubber(s) 648, the $CO_2$ stream 646 or 647 may undergo further separation upstream of the pressurization device 645 to remove gases, such as methane or hydrogen, sometimes found in this stream using techniques known for the purification of natural gas and biogas (not shown in figure). Such techniques may allow the recovery of the methane or hydrogen, which may be exported, used (recycled) in the process, or burned to provide energy as process heat. Where the recovery of methane and/or hydrogen may not be desired, methane and hydrogen can also be sent, for instance, to a biofiltration bed to be converted into $CO_2$. This process may be simple and economical, and provide the ability to remove these inert gases, which may result in savings in compression energy.

When the ion-exchange beds 633 are regenerated, hydrogen ions, from the carbonic acid produced from the pressurized $CO_2$ 643A may replace the other cations that may have been absorbed on to the bed, such as, but not limited to, sodium, potassium, ammonium. Because excess $CO_2$ may be added, after pressure is released, some $CO_2$ may be released from the solution leaving behind the stream containing the cations, which may remain in solution mostly as bicarbonates.

Then this bicarbonate stream 649 may be passed through a $CO_2$ degasifier 618B (e.g., stripper), which may further release $CO_2$ and converts some or all of the bicarbonates into carbonates. These carbonates and/or bicarbonates may be used as buffer 613, and recycled to the fermentation 603 for use to control pH, except for some amount may require purge in order to avoid accumulation of the cations in the system. The $CO_2$ 650 that may be released after the pressure is decreased by depressurization 651, and/or from the degasifier 618B may be recycled to be pressurized/compressed (e.g., 645).

Figure 7:
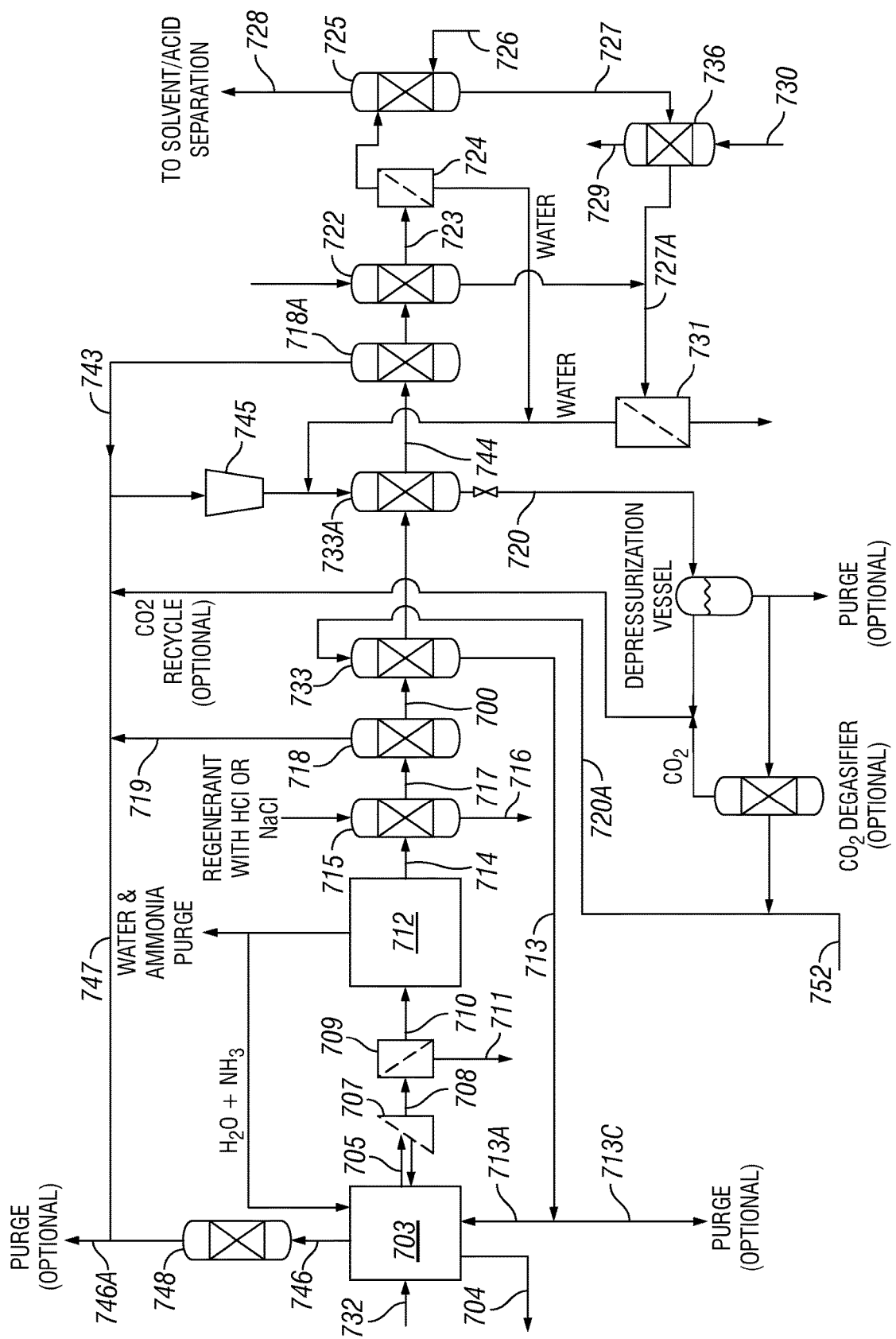
FIG. 7 shows a process that includes integration of carboxylic acid (VFA) salts production in anaerobic fermentation and conversion of VFA salts to acids using ion exchange with high-pressure $CO_2$ for regeneration and with anion-exchange as a concentration/purification step, according to embodiments of the disclosure.

FIG. 7 shows a process comparable to and like that of FIG. 6, and illustrates an anion exchange step may be used. The anion exchange 733 may concentrate and purify the VFA salts of broth 705, and convert salts substantially or completely into a single cation prior to entering the main $CO_2$-regenerated cation-exchange system 733A (for illustration, FIG. 7 shows sodium as the cation of choice). An anion exchange may extract negatively charged ions (i.e., anions) from the solution. Such ions may include the anions of the VFA salts. This step can be used in addition to or instead of the dewatering step or steps of embodiments of the disclosure, including those of FIGS. 6 and 7.

From the anion exchange step 733, buffer 713 may be obtained and recycled to the fermentation 703. In some aspects, some of this buffer stream 713 may be purged 713C. The base 720, 720A generated from the regeneration of the main cation exchange system 733A, which may be substantially one single cation (e.g., sodium), may be used to regenerate the anion exchange bed 733. Some make-up 752 of the single cation (e.g., sodium hydroxide) may be added as needed. In some aspects, the cation stream exiting the main cation-exchange system 733A may be concentrated prior to being used as the regenerant in the anion exchange system 733.

When medium-chain fatty acids (e.g., caproic, enanthic, caprylic, pelargonic acid, combinations thereof, acids larger than C6, in the range of C6-C9, etc.) are present in sufficiently high concentrations, after acidification as described herein, these acids may phase out of solution and they may be selectively separated by a simple liquid-liquid separation step, while the short-chain fatty acids, such as, but not limited to, acetic, propionic, butyric, pentanoic or any combination thereof, may remain in the aqueous phase.

The acidified stream/broth 744 may continue to extraction 725 in accordance with embodiments described herein, and as illustrated by example in FIGS. 6 and 7. If the medium-chain fatty acids are the product and it is desired for the shorter-chain fatty acids to undergo elongation, the short-chain fatty acids still present in the aqueous phase may be recycled to the fermentation 703. In this sense, the short-chain fatty acids may continue the elongation process. As such, liquid-liquid extraction is not needed or would be considered as optional. In FIGS. 6-7, similar reference numerals denote similar parts/apparatuses with similar functions and should be thus understood.

Integration of Carboxylic Acid Production with Liquid-Liquid Extraction Under High-Pressure $CO_2$ Embodiments of the disclosure pertain to a process for concentration of the fermentation broth with reverse osmosis (RO), which may use high pressures, and with acidification and acid extraction under high pressure $CO_2$.

Figure 8:
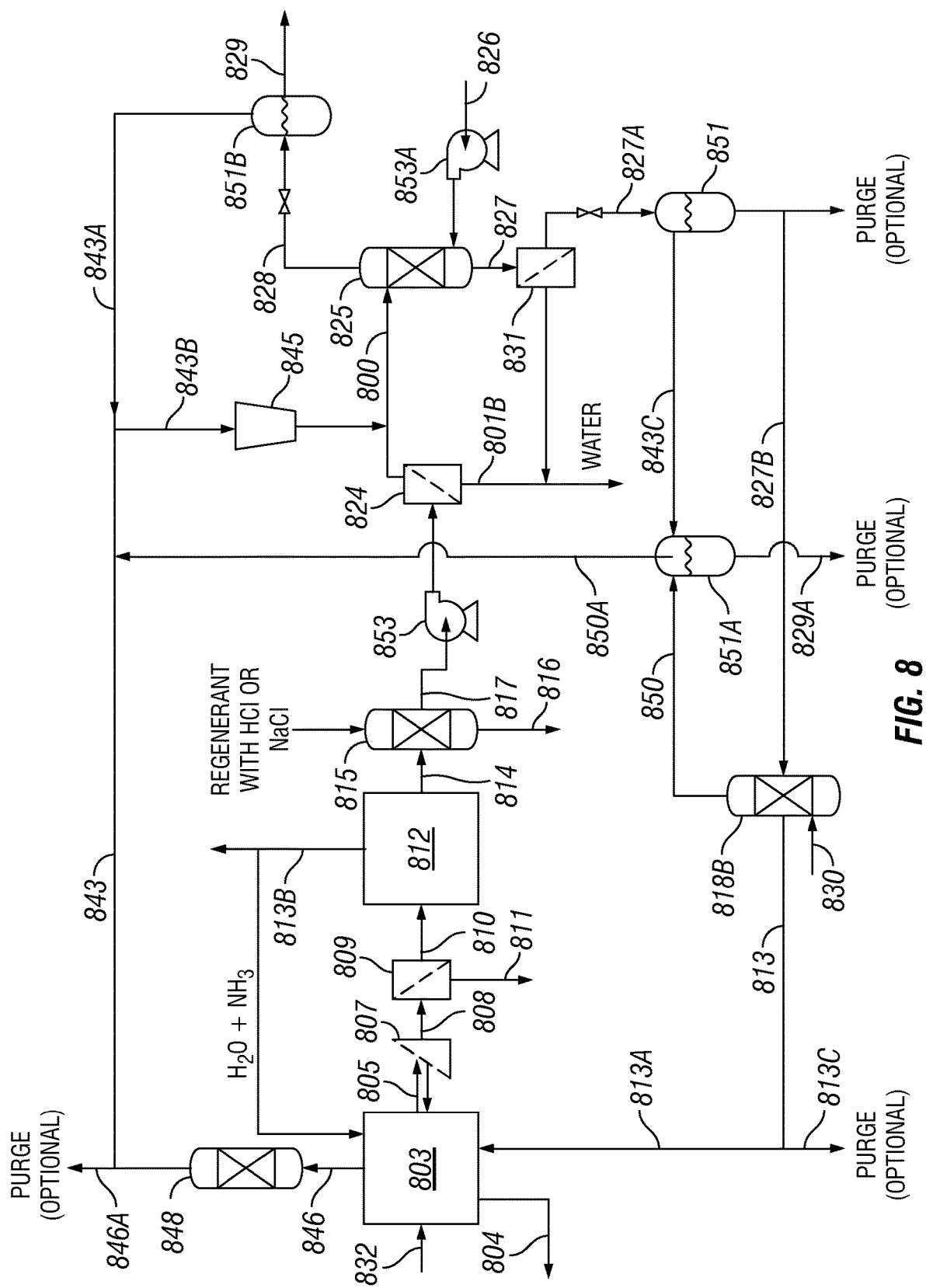
FIG. 8 shows a process that includes integration of carboxylic acid (VFA) salts production in anaerobic fermentation and the conversion of VFA salts to acids using liquid-liquid extraction under high-pressure $CO_2$, according to embodiments of the disclosure.

FIG. 8 shows the integration of the production of carboxylic acid (volatile fatty acids—VFA) salts in an anaerobic fermentation process, acidification of the salts with high-pressure $CO_2$, and liquid-liquid extraction for recovery of organic acids produced. The biomass 832 to be fermented into VFAs may be fed to a fermentation system 803. Such fermentation system 803 may be any vessel or system of vessels of different configurations such as, but not limited to, those described in U.S. patent application Ser. No. 12/708, 298, incorporated by reference in its entirety for all purposes. System 803 may include other peripheral devices such as, but not limited to, grinders, pumps, heat exchangers for keeping the adequate temperature in the fermentation, and liquid/solid separators such as, but not limited to, screw-presses, belt presses, plate-and-frame presses, screens and centrifuges.

Microorganisms may convert the biomass into VFAs, then the VFA's get neutralized with a buffering agent (e.g., sodium carbonate), which may result in production of VFA salts in fermentation broth 805. Some of the biomass 832 may be unreacted and may be removed from the system 803 as undigested residue or digestate 804. The fermentation broth 805 that exits the fermentation step or unit(s) 803, which may contain VFA salts, may be sent through a screen (not shown in figure) to remove solids and/or sent to clarification 807 to produce a clean (e.g., solids/free, clarified) effluent 808. The clarification process 807 may be, but is not limited to, micro- or ultra-filtration membranes, flocculation, coagulation, dissolved-air flotation, electrocoagulation, combinations thereof, and so forth. The cleaner effluent 808 from clarification 807 may go through membrane cleaning 809 (e.g., nanofiltration, etc.), which may help to clean proteins and other impurities, thus generating a concentrate stream 811, which may be exported as a by-product or it may be recycled to the fermentation (not shown in figure).

The clean permeate 810 (or broth 805) containing the VFA salts may undergo further dewatering or concentration 812. Such concentration 812 may be done using methods that may include reverse osmosis (RO), evaporation, electrodialysis (CED), electrodionization (EDI), combinations thereof, and the like. The water and other compounds that may be removed during dewatering or concentration 812 may be recycled via stream 813 back to fermentation 803 via 813A, or may be optionally purges via 813C. The concentrate 814 may be sent to a softener ion exchange bed 815 where multi-valent cations such as magnesium, calcium, iron, and others, which tend to form insoluble salts, are removed if necessary. The softener bed 815 may be regenerated with sodium or potassium chloride, hydrochloric acid, and so forth, which may result in a stream of multi-valent cation chlorides (e.g., calcium, magnesium, iron chloride, etc.) 816. This may be used to prevent these ions from clogging/fouling the liquid-liquid extraction bed as they precipitate.

The multi-valent-cation free stream 817 from the softener bed 815 may be pressurized (such as with pump 853) to raise its pressure, and may be sent to an RO unit system 824, where water may be removed via stream 801B. Without lowering the pressure, the concentrated stream 800 may be sent to liquid-liquid extraction 825. The $CO_2$ 843B, which may be obtained from the carbonates that are used as buffering agent to neutralize the acids produced in the fermentation, may be pressurized using a pressurization device (e.g., gas compressor, etc.) 845, and may be injected at this pressure into the stream 800 and/or directly into the extraction system 825. The use of high-pressure $CO_2$ may result in acidification of the broth (e.g., 800, 805, etc.) that contains the VFA salts, resulting in conversion of VFA salts to acids. The acids may be extracted into an appropriate extracting solvent 826, which may also pressurized (such as by pump 853A) to the appropriate pressure as it enters the extraction system 825.

The extracting solvent stream 828 containing the acids (i.e., the extract) may be depressurized via, for example, a valve and sent to vessel 851B before sending it upstream to separate it from the acids it has extracted 829. The acid-lean raffinate 827 may be sent to another RO 831 for further dewatering prior to lowering the pressure. The raffinate stream 827, 827A may then be depressurized via, for example, a valve and sent to depressurization vessel 851. From the depressurization of the extract stream 828 and raffinate stream(s) 827, 827A, $CO_2$ 843A, 843C may be released, respectively and may resultantly be recycled and/or be recompressed.

The depressurized acid-lean raffinate 827B may contain all the cations (e.g., sodium, potassium, ammonium) from the fermentation. These cations may be substantially in the form of bicarbonates. This stream 827B may be degasified via unit or system 818B to remove $CO_2$ 850, which may also allow some or all the bicarbonates to become carbonates. Such a degasifying system 818B may be, but not limited to, a steam stripper. In this degasifier 818B, at least some of the solvent, if less volatile than the acids, may also be recovered. This stream 850 that may include $CO_2$, solvent, and water, may be sent to a liquid trapping vessel 851A, such that $CO_2$ may disengage. Any such $CO_2$ 850A may be recycled and/or be re-pressurized, and the solvent 829A may be sent downstream to the solvent/acid separation system to be recovered.

From the fermentation 803, excess $CO_2$ 846A may be generated from the biological conversions, in addition to the $CO_2$ 843 generated from the carbonates. This excess $CO_2$ 846A may be purged from the system and sent to an odor control system (e.g., a biofilter). Prior to compression, $CO_2$ 846 may be passed through a scrubber(s) 848 to remove certain impurities such as, but not limited to, volatile acids and hydrogen sulfide.

In addition to or instead of scrubbers, the $CO_2$ stream 846 or 843 may undergo further separation upstream of the pressurization device 845 to remove methane or hydrogen that may be found therein via techniques and processes known for the purification of natural gas and biogas (not shown in figure). Such techniques may allow the recovery of the methane or hydrogen, which may be exported, used somewhere else in the process, burned to be used as process energy (heat), etc. Methane and hydrogen may also be sent, for instance, to a biofiltration bed to be converted into $CO_2$, which may also fulfill the purpose of removing inert gases, and result in savings in compression energy.

If the extracting solvent 826 is a very non-polar compound, it will absorb $CO_2$ because of the non-polar nature of $CO_2$; therefore, a degasifying system may be used in the extracting solvent recovery system downstream (not shown in figure).

The degasified raffinate stream 813 exiting the degasification system 818B which may contain all cations in the form of carbonates and bicarbonates, may be used as the buffering stream 813A that may be added to the fermentation 803 to control pH. At least a portion of this stream 813 may be purged to avoid accumulation of these cations in the system. In some embodiments, turbines in the streams that are being depressurized may be coupled to the pumps/compressors in the streams that are being pressurized to recover some of the energy.

When medium-chain fatty acids (MCFAs), such as, but not limited to, caproic, enanthic, caprylic, pelargonic acid, acids larger than C6, acids in the range of about C6-C9, combinations thereof, etc. are present in sufficient concentrations, after the acidification in accordance with embodiments described herein, these acids phase out of solution. As such, they may be selectively separated by a simple liquid-liquid separation step, while any short-chain fatty acids, such as, but not limited to, acetic, propionic, butyric, pentanoic or any combination thereof, which may remain in the aqueous phase, may continue to extraction in accordance with embodiments described herein.

If MCFAs are the desired product, and it is desired for shorter-chain fatty acids to undergo elongation, any shorter-chain fatty acids still present in the aqueous phase may not be extracted, and may be recycled to the fermentation in order to continue the elongation process. As such, a liquid-liquid extraction system is not needed or would be considered as optional (but only a liquid-liquid separation vessel or system). This particular aspect is illustrated by the process shown in FIG. 9.

Figure 9:
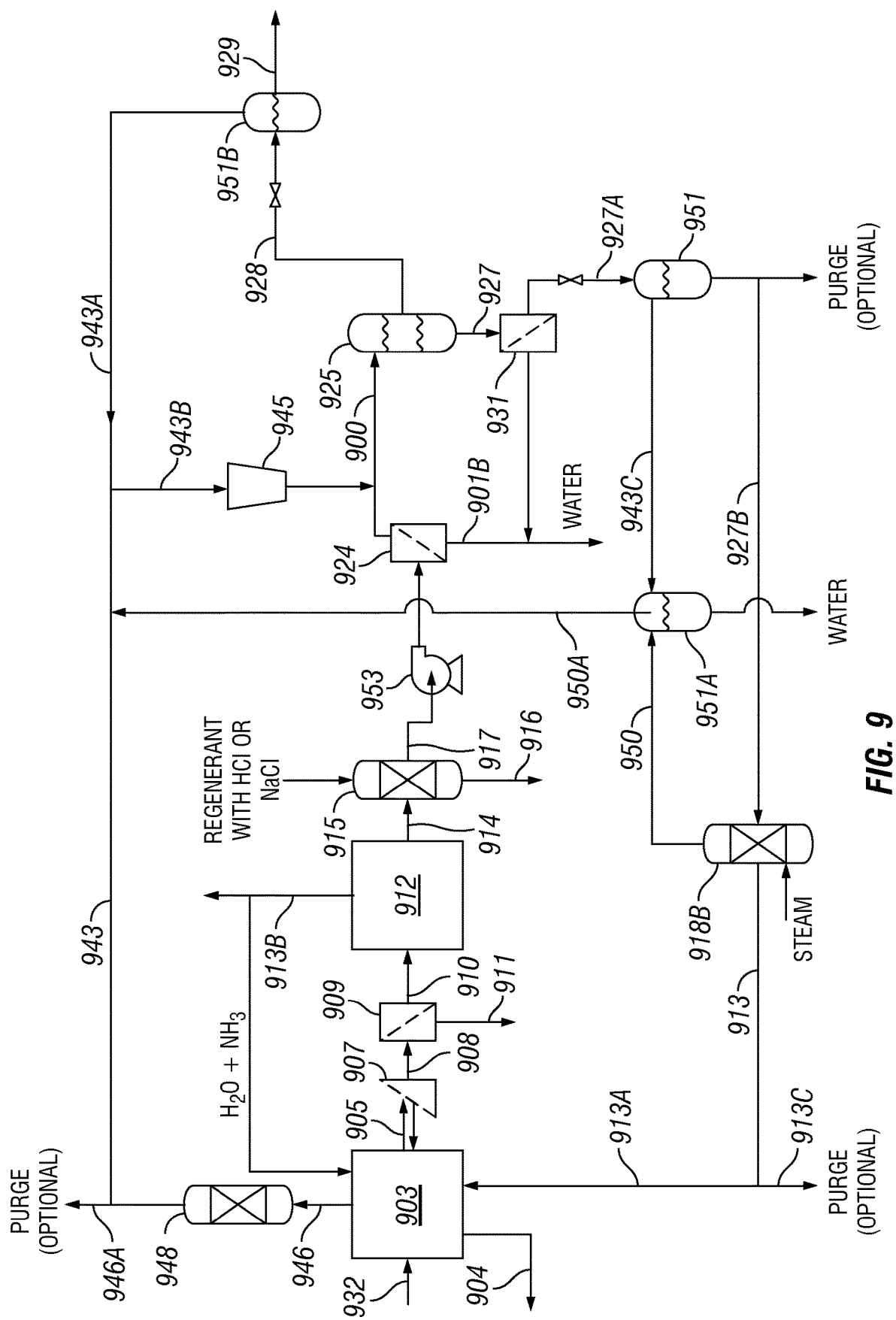
FIG. 9 shows a process that includes integration of carboxylic acid (VFA) salts production in anaerobic fermentation and conversion of VFA salts to acids under high-pressure $CO_2$, where the water-insoluble medium-chain fatty acids (MCFAs) produced in fermentation phase out of solution and are separated and recovered, according to embodiments of the disclosure.

FIG. 9 shows a process comparable to and like that of FIG. 8, but with MCFAs as the desired product. As $CO_2$ 943B is pressurized 945 and injected into the pressurized concentrated broth stream 900, the water-insoluble MCFAs 928 phase out and are separated from the aqueous phase 927 in a unit such as, but not limited to, a liquid-liquid separation vessel 925. The water-soluble short-chain fatty acids, on the other hand, remain in the aqueous phase 927 with the ions and other impurities and are recycled to the fermentation system 903 together with the buffer used to control pH 913.

Advantageously in embodiments such as those shown in FIGS. 8 and 9, the RO, dewatering, and the extraction may occur at the same pressure as the $CO_2$ acidification, thus saving pumping energy. In FIGS. 8-9, similar reference numerals denote similar parts/apparatuses with similar functions and should be thus understood.

Liquid-Liquid Extraction

With general regard to FIG. 2 through FIG. 8, once VFA salts are converted into acids using any of the techniques described herein, the acids may be extracted from the aqueous solution. Such extraction may occur by liquid-liquid extraction with use of a wide variety of solvents. Solvents such as MTBE and ethyl acetate are known to extract acetic acid, n-butanol, n-pentanol, cyclohexanone, methylisobutyl ketone are known to extract propionic acid, amines and phosphine oxides are also known to extract volatile fatty acids. Medium-chain fatty acids (MCFAs) with low water solubility may be used as a solvent.

These extracting solvents may be used in recovering VFAs from aqueous solutions followed then by solvent/acid separation for solvent recovery. Several schemes for extraction and solvent recovery and separation from the carboxylic acids have been proposed and any of such can be used, without limitation, to extract and recover the VFAs from the aqueous solution. In embodiments, integration of liquid-liquid extraction may include the use of extracting solvents that may be produced within the process, which provides for robust economics in addition to independence on the prices of extraneous solvents.

The use of MCFAs with low water solubility, which may be produced in the fermentation itself, is an example of a process that may use solvents or compounds produced within the system, and as a result avoid the use of extraneous solvents. After the extraction, the MCFAs may be separated from the short-chain fatty acids, by techniques or processes such as distillation. The short-chain fatty acids may be part of the product, and some of the MCFAs may be removed as product to avoid accumulation as they are also produced in the fermentation. At least some MCFAs may be recycled to the extraction to repeat the extraction process.

Other examples of processes that use compounds that are produced within the process as extracting solvents are the integration of VFA extraction with ketones with the production of ketones from those VFAs and the integration of VFA extraction with ethyl acetate and the production of ethyl acetate from acetic acid, which is one of the VFAs produced in the system.

Figure 10:
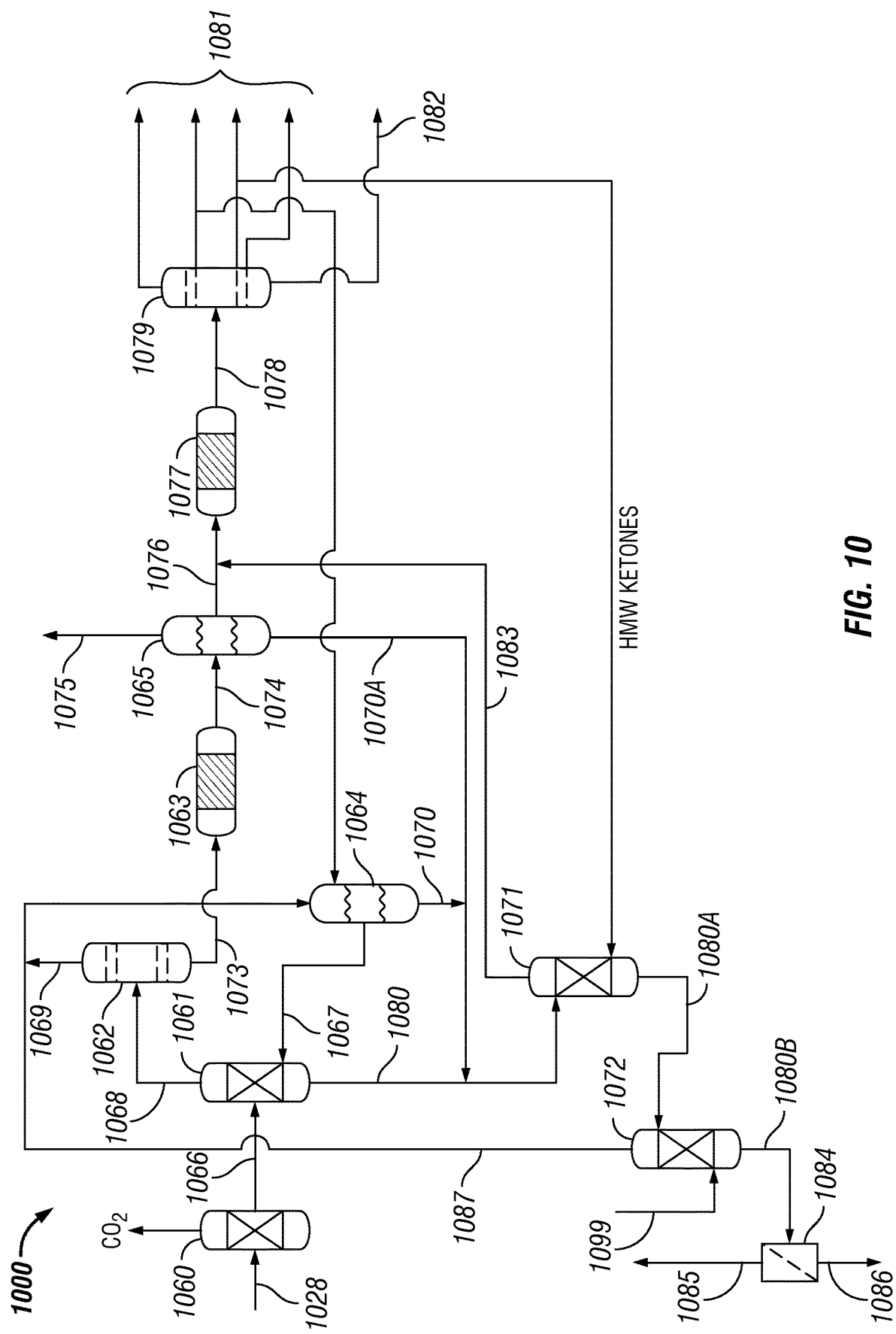
FIG. 10 shows a process that includes integration of carboxylic acid (VFA) extraction with low-molecular-weight ketones as extracting solvent and the catalytic conversion of the VFAs into ketones, according to embodiments of the disclosure.

Integration of Liquid-Liquid Extraction with Ketones in a Process that Produces Ketones from VFAs In accordance with embodiments disclosed herein, the production of ketones from VFAs has a synergistic effect, as the ketones, which are known to be good extracting solvents, may be used in the extraction process. The ketones may be produced from catalytic conversion of acids over certain catalysts such as, but not limited to, aluminum oxide, zirconium oxide, titanium oxide, cerium oxide, manganese oxide and magnesium oxide. FIG. 10 illustrates an example of this type of process.

As shown and made apparent, the aqueous solution 1028 acidified using the methods described herein, which may include VFAs, $CO_2$, as well as other ions such as, but not limited to, $Na^+$, $K^+$, $Cl^-$, $PO_4^{3-}$, etc. (i.e., ions that do not tend to form insoluble salts, as may be ensured by their removal in a softening step, shown by way of illustrative example in FIGS. 2 through 8, which may help avoid fouling) may be fed to the system 1000. This stream 1028 may undergo $CO_2$ (and/or other volatile species, gases, etc.) removal by usage of, for example, a stripper 1060 or other means known to those skilled in the art.

The resulting liquid 1066, which may be $CO_2$-free liquid, may be sent to an acid extraction column 1061, where it may be contacted by a stream 1067 comprised of low-molecular-weight (LMW) ketones, such as acetone, butanone, pentanone, hexanone, etc. In an embodiment, the LMW ketones may be butanone and pentanone (C4-C5 ketones). Butanone and pentanone have a lower boiling point than acetic acid, the lightest VFA, which may allow for simple separation and recovery of these ketones in distillation. In addition, butanone and pentanone have a very high distribution coefficient with acetic acid and the other higher acids, which may make these ketones ideal for their extraction.

After extraction, the product stream 1068, which may include LMW ketones, VFAs, and some water, may be sent to a distillation column 1062 where LMW ketones and water may be separated from the VFAs. The LMW ketones and water recovered in the distillate 1069 from distillation unit 1062 may be sent to an organic liquid-aqueous liquid (OLAL) separator 1064, where two phases (one organic and one aqueous) may form. The organic phase 1067 with the LMW ketones may be sent back to the acid extraction unit 1061, and thus may serve as the extracting solvent. The aqueous phase 1070, which may be mostly water, may be sent to a Ketone Recovery Extraction Unit 1071 or directly to a steam stripper 1072, in accordance with embodiments described herein. Any VFAs recovered in bottoms 1073 of the distillation unit 1062 may be sent to a catalytic reactor 1063 containing catalysts such as, but not limited to, aluminum oxide, zirconium oxide, titanium oxide, cerium oxide, manganese oxide, magnesium oxide, or combinations thereof, such that VFAs may be converted to ketones, water, and carbon dioxide.

The reactor product stream that may include ketone, water, and $CO_2$ stream may be sent to a separator (e.g., gas-organic liquid-aqueous liquid (GOLAL) separator, etc.) 1065, where CO2, the organic phase, and the aqueous phase may be separated. $CO_2$ may be vented or recycled via stream 1075 within any process described herein, including for purposes such as high-pressure acidification illustrated by way of example in FIGS. 6 through 8. The aqueous phase via stream 1070A, which may contain some LMW ketones (e.g., acetone, butanone, etc.), may be joined with the aqueous raffinate 1070 exiting the OLAL separator unit 1064, and may be sent to the Ketone Recovery Extraction Unit 1071. The organic phase stream 1076 exiting the GOLAL separator unit 1065, which may include mostly ketones, may be sent to a polishing catalytic reactor 1077 containing ketonization catalyst, where any remaining VFAs (if any at all) may be converted.

The resulting ketone stream 1078 from the polishing reactor 1077 may be sent to ketone distillation 1079, which may be one or several unit, where separation of ketones occurs. As an example of how this distillation would work may be described with reference to the following streams:
1. Acetone
2. C4-C5 ketones (e.g., butanone and pentanone), which may be the LMW ketones to be recycled as extracting solvent for the VFAs in the acid extraction unit 1061. This stream may contain some water as well.
3. C6-C7 ketones (e.g., hexanone and heptanone)
4. C8-C9 ketones (e.g., octanone and nonanone), may be the high-molecular-weight (HMW) ketones to be recycled as extracting solvent for the LMW Ketone Recovery Extraction Unit 1071
5. Higher ketones (e.g., decanone, undecanone, dodecanone, tridecanone)
6. Tars (heavy compounds)

As mentioned, some of the LMW ketones (e.g., C4-C5 ketones) separated may be recycled to the Acid Extraction unit 1061, which may help to make up for any losses of LMW ketones in the water raffinate stream 1080 from this extraction unit 1061. Some of the HMW ketones (e.g., C8-C9 ketones) may be sent to the Ketone Recovery Extraction unit 1071, where they may be used to extract LMW ketones from the water raffinate stream 1080 coming from the Acid Extraction unit 1061.

LMW ketones and/or HMW ketones that do not get recycled may exit the system via ketone product(s) 1081. Tars stream 1082 may exit the system 1000 from the bottom of the distillation tower(s) 1079. Further conversion of the LMW and HMW ketone product may occur, where, for instance, the ketones are converted into fuels as in accordance with embodiments disclosed in U.S. patent application Ser. No. 12/629,285 and U.S. patent application Ser. No. 12/745,226, incorporated by reference in entirety for all purposes.

The water raffinate 1080 from the Acid Extraction unit 1061 may include dissolved LMW ketones, unrecovered VFAs, and ions (e.g., $Na^+$, $K^+$, $Cl^-$, etc) coming from upstream. To recover the LMW ketones, a good extraction solvent are the HMW ketones (e.g., C8-C9 ketones, etc.). The HMW ketones may be useful as the extraction solvent as a result of low solubility with water, high distribution coefficient, and good flowability. These HMW ketones, which may come from the ketone distillation tower(s) 1079, may be used to recover the LMW ketones in the water raffinate 1080 in the Ketone Recovery Extraction unit 1071.

Because the raffinate 1080 may include VFAs, these VFAs might be extracted by the HMW ketone stream. As such, this stream 1083 coming out of the Ketone Recovery Extraction unit 1071 may be recycled to the front end of the polishing catalytic ketone reactor 1077. The raffinate 1080A from the Acid Extraction unit 1061 may be sent to a stripping operation or unit 1072 (e.g., steam stripper), which may be configured to operate and recover any LMW ketones still present. This stripping operation 1072 may be performed in addition to or instead of the LMW Ketone recovery extraction with the HMW ketones. The LMW ketones (with some water) 1087 recovered in the steam stripping unit 1072 may be sent to the OLAL separator 1064 together with the distillate 1069 coming off of the Solvent Distillation column 1062.

The water raffinate 1080A from the Ketone Recovery Extraction unit 1071 and/or the stripped stream 1080B from the steam stripper 1072, which may be lean in VFAs and ketones and/or may contain mostly the ions (e.g., $Na^+$, $K^+$, $Cl^-$, etc) coming from upstream, may be sent to an RO unit or system 1084 for concentration and to recover some clean water. The recovered water stream 1085 may be used in other parts of the process, such as the clean water feed to the EAU unit in accordance with embodiments disclosed herein (see FIGS. 2 through 5), or for the regeneration of the cation exchange unit with high-pressure $CO_2$ (see FIGS. 6 and 7). In embodiments, the water may be treated for outfall. The concentrated raffinate 1086 obtained from the RO unit 1084 may be purged from the system as waste. In embodiments, the concentrated raffinate 1086 may be sent upstream to be used as the regenerant for the softener unit (see FIGS. 2 through 5).

The raffinate from the LMW Ketone Recovery Extraction unit 1080A and/or the stripped stream 1080B from the steam stripper, prior to concentration or after concentration in the RO unit 1084, may be recycled to the fermentation (e.g., FIGS. 2-9). This may be especially appropriate if its components (e.g., $Na^+$, $K^+$, $Cl^-$, etc) may be purged elsewhere (e.g., with the fermentation undigested residue) in order to avoid their accumulation in the process, or by purging some of the base produced in the EAU unit (see FIGS. 2 through 5), in the regeneration of the ion exchange resin (see FIGS. 6 and 7), or in the solvent extraction performed under high-pressure $CO_2$ (see FIG. 8).

For extraction under high-pressure $CO_2$ (FIG. 8), the raffinate stream may be used as the buffer that may be recycled to the fermentation to control pH after purging a portion of it. Recycling the raffinate to the fermentation is advantageous because it recycles any unconverted acids, ketones and the buffer in the case of the process in FIG. 8, avoiding their loss.

When referring to particular product streams herein, it should be understood that, although the primary product(s) may be described, other products may exist in the product stream. For example, if as LMW ketones for extraction of the VFAs, the preferred butanone-pentanone (C4-C5) ketones are used, the bulk of the C4-C5 ketone stream might comprise butanone and pentanone, but it may also contain, in addition to some water, small quantities of acetone, or other ketones.

For the HMW ketone stream used to extract LMW ketones from the aqueous stream, if C8-C9 ketones (octanone and nonanone) are used, this stream will be comprised mostly of C8 and C9 ketones, but it may also contain small quantities of VFAs, and other lower-molecular-weight ketones, such as, but not limited to, pentanone, hexanone and heptanone. The tars, which may be predominantly very large molecular weight compounds, may also contain some ketones (e.g., decanone, undecanone, dodecanone, tri-decanone, etc.), and other impurities such as nitrogenated compounds. The water raffinate exiting the extraction unit may contain, in addition to the ions mentioned above (e.g., $Na^+$, $K^+$, $Cl^-$, etc), impurities such ammonia, proteins and others.

Figure 11:
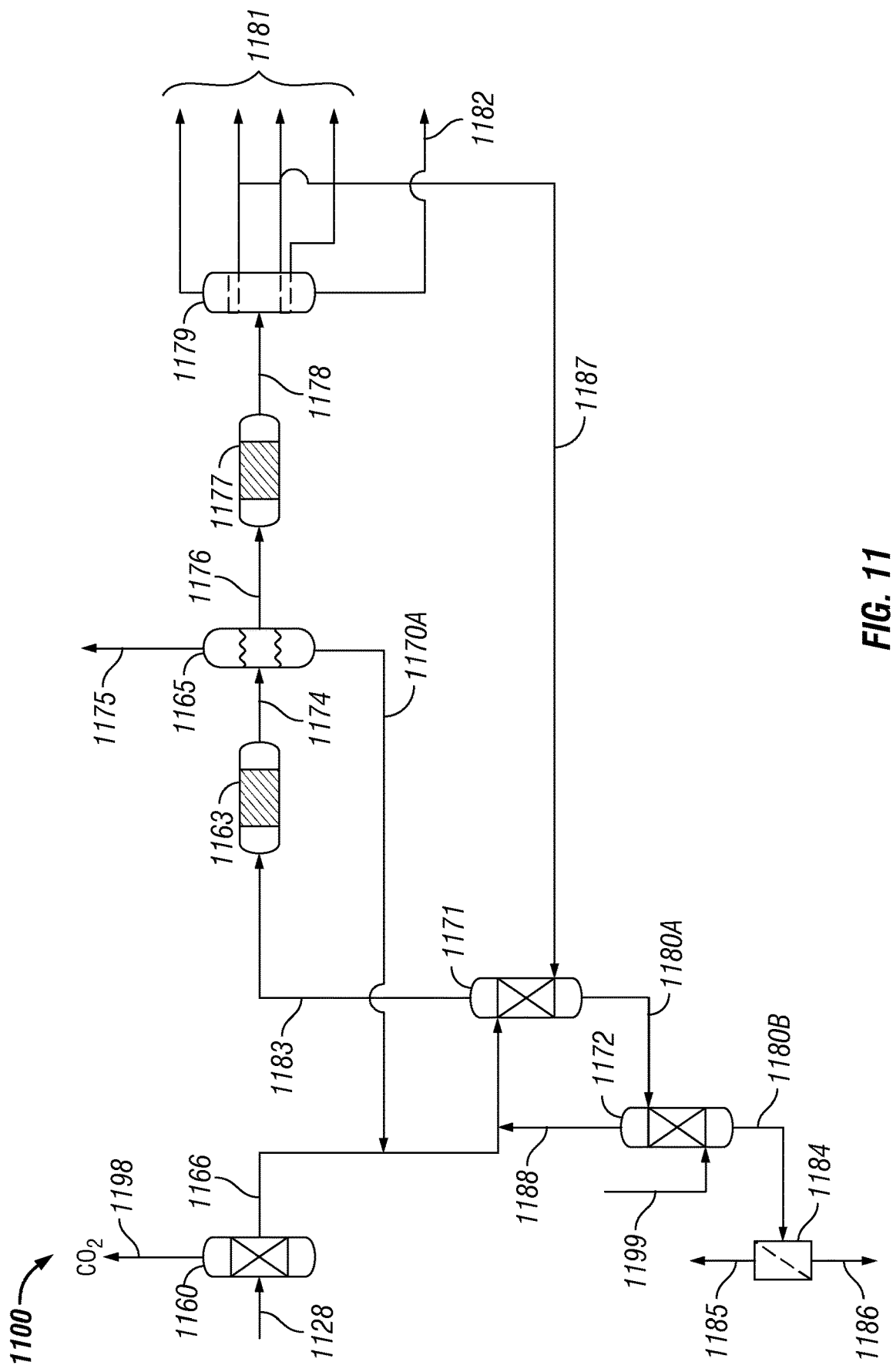
FIG. 11 shows a process that includes integration of carboxylic acid (VFA) extraction with high-molecular-weight ketones as extracting solvent and the catalytic conversion of the VFAs into ketones, according to embodiments of the disclosure.

FIG. 10 illustrates an embodiment of the disclosure that makes use of LMW ketones (e.g., C4-C5 ketones) as the extracting solvent for the VFAs, whereas FIG. 11 illustrates use of HMW ketones (e.g., C8-C9 ketones) as the extracting solvent for the VFAs. FIG. 11 shows another method for integration of VFA extraction from an aqueous solution with the conversion of VFAs to ketones.

FIG. 11 illustrates the aqueous phase 1128, which may contain VFAs from the conversion of the salts to the acid form, may enter the process (or system) 1100. Other species, such as $CO_2$, $Na^+$, $K^+$, $Cl^-$, and other impurities, might also be present within phase stream 1128. This stream 1128 may be sent to a unit 1160 where $CO_2$ and other volatile components may be removed using, for example, a stripper or other device known to those skilled in the art. The resultant liquid (which may be substantially $CO_2$-free) 1166 may be sent to an acid/Ketone Recovery Extraction unit 1171 where it may be contacted with HMW ketones (e.g., hexanone, heptanone, octanone, nonanone, decanone, undecanone, etc. but preferably octanone, nonanone). These HMW ketones are suitable for extraction of HMW VFAs.

The resulting HWM ketone stream 1183, which may include the extracted acids, may be sent to a catalytic reactor 1163. The catalytic reactor 1163 may include, contain and/or be configured with catalysts such as, but not limited to, aluminum oxide, zirconium oxide, titanium oxide, cerium oxide, manganese oxide, magnesium oxide, and combinations thereof, where at least a portion of the HWM ketone stream 1183 may be converted to ketones, water, and carbon dioxide. This ketone/water/$CO_2$ stream 1174 may be sent to a gas-organic liquid-aqueous liquid (GOLAL) separator 1165, where gases, such as $CO_2$, the organic phase, and the aqueous phase may be separated. The gases (e.g., $CO_2$) by way of stream 1175 may be vented or recycled within the process for other purposes such as what is shown in FIGS. 6 through 8. The aqueous phase 1170A, which may contain LMW ketones, such as, but not limited to, acetone and butanone, may be joined to the aqueous stream 1166 containing the VFAs and sent to the acid/Ketone Extraction Unit 1171.

The organic phase stream 1176, which may include ketones and unconverted VFAs, may be sent to a polishing catalytic reactor 1177. The reactor 1177 may contain ketonization catalyst, such that remaining VFAs may be converted. The resulting ketone stream 1178 may exit the polishing reactor 1177, and may be sent to ketone distillation or unit 1179, where separation of ketones may take place in accordance with embodiments described herein (see FIG. 10). HMW ketones of the proper size (e.g., octanone and nonanone) separated by distillation may be recycled via recycle stream 1187 to the Acid/Ketone Extraction unit 1071 to act as extracting solvent.

Ketones may exit the system or process 1100 via ketone product stream(s) 1181. From the bottom of the distillation system(s) 1179, tars 1182 may be separated as their own stream. Further conversion of the LMW and HMW ketone product may occur, where, for instance, the ketones are converted into fuels in accordance with embodiments described in U.S. patent application Ser. No. 12/629,285 and U.S. patent application Ser. No. 12/745,226, incorporated by reference in entirety for all purposes.

The water raffinate 1180A from the Acid/Ketone Extraction unit 1171 may contain some LMW ketones; therefore, at least some water raffinate 1180A may be sent to a system 1172, such as, but not limited to, a steam stripper, which may recover LMW ketones. The stream 1188 from the stripper 1172, which may contain LMW ketones (with some water), may be sent to the front end of the Acid/LMW Ketone Extraction unit 1171.

Any resulting aqueous stream 1180B from the stripper 1172, which may include VFAs, ketones, and ions (e.g., $Na^+$, $K^+$, $Cl^-$, etc), may be sent to an RO system 1184 for concentration, and to recover some clean(ed) water, which may be used in other parts of the process. For example, the clean water 1185 may be fed to the EAU unit (see FIGS. 2 through 5), or may be used for regeneration of the cation exchange unit with high-pressure $CO_2$ (see FIGS. 6 and 7). In an embodiment, the cleaned water 1185 may be treated for outfall. The concentrated raffinate 1186 obtained from the RO unit 1184 may be purged from the system 1100 as waste, or may be used as the regenerant for the softener unit(s) (see FIG. 2 through 5).

Although not shown, at least some of the raffinate 1180 from the Acid/Ketone Extraction unit 1171, prior to and/or after concentration in the RO unit 1184, may be recycled to the fermentation (of FIGS. 2 through 8) if its components (e.g., $Na^+$, $Cl^-$, etc) may be purged to avoid accumulation in the process, such as with the fermentation undigested residue or, in embodiments, the base produced in the EAU unit (FIGS. 2 through 5), in the regeneration of the ion exchange resin (FIGS. 6 and 7), or in the solvent extraction performed under high-pressure $CO_2$ (FIG. 8), may be purged.

For the extraction under high-pressure $CO_2$ (FIG. 8), this raffinate stream 1180 may be used as the buffer, which may be recycled to the fermentation to control pH after purging a portion of it. Recycling the raffinate to the fermentation is advantageous because it recycles any unconverted acids, ketones and the buffer, such as in the case of the process in FIG. 8, which may reduce or avoid their loss.

As mentioned, streams described may not be clean cuts, such that streams may contain small quantities of the other compounds in the system and other impurities. For example, for the HMW ketone stream used to extract VFAs and LMW ketones, if C8-C9 ketones (octanone and nonanone) are used, this stream may include C8 and C9 ketones, quantities of VFAs, other lower-molecular-weight ketones (e.g., pentanone, hexanone, heptanone, etc.), other higher-molecular-weight ketones (e.g., decanone, undecanone, dodecanone, etc.), and other impurities. The tars may include very large molecular weight compounds, ketones (e.g., decanone, undecanone, dodecanone, tri-decanone, etc.), and other impurities such as nitrogenated compounds. The water raffinate exiting the Acid/LMW Ketone Extraction unit may contain ions (e.g., $Na^+$, $K^+$, $Cl^-$, etc), and impurities such ammonia, proteins and others. In FIGS. 10-11, similar reference numerals denote similar parts/apparatuses with similar functions and should be thus understood.

4.1 Integration of Liquid-Liquid Extraction with Ethyl Acetate in a Process that Produces Ethyl Acetate from VFAs Acetic acid produced in mixed VFA anaerobic fermentation may be used to produce ethyl acetate. Known methods for ethyl acetate production from acetic acid may be used, such as the production of ethyl acetate from acetic acid via esterification of acetic acid with ethanol, or the reaction of ethylene with acetic acid to make ethyl acetate. Ethyl acetate may be a good extracting solvent for VFAs.

Figure 12:
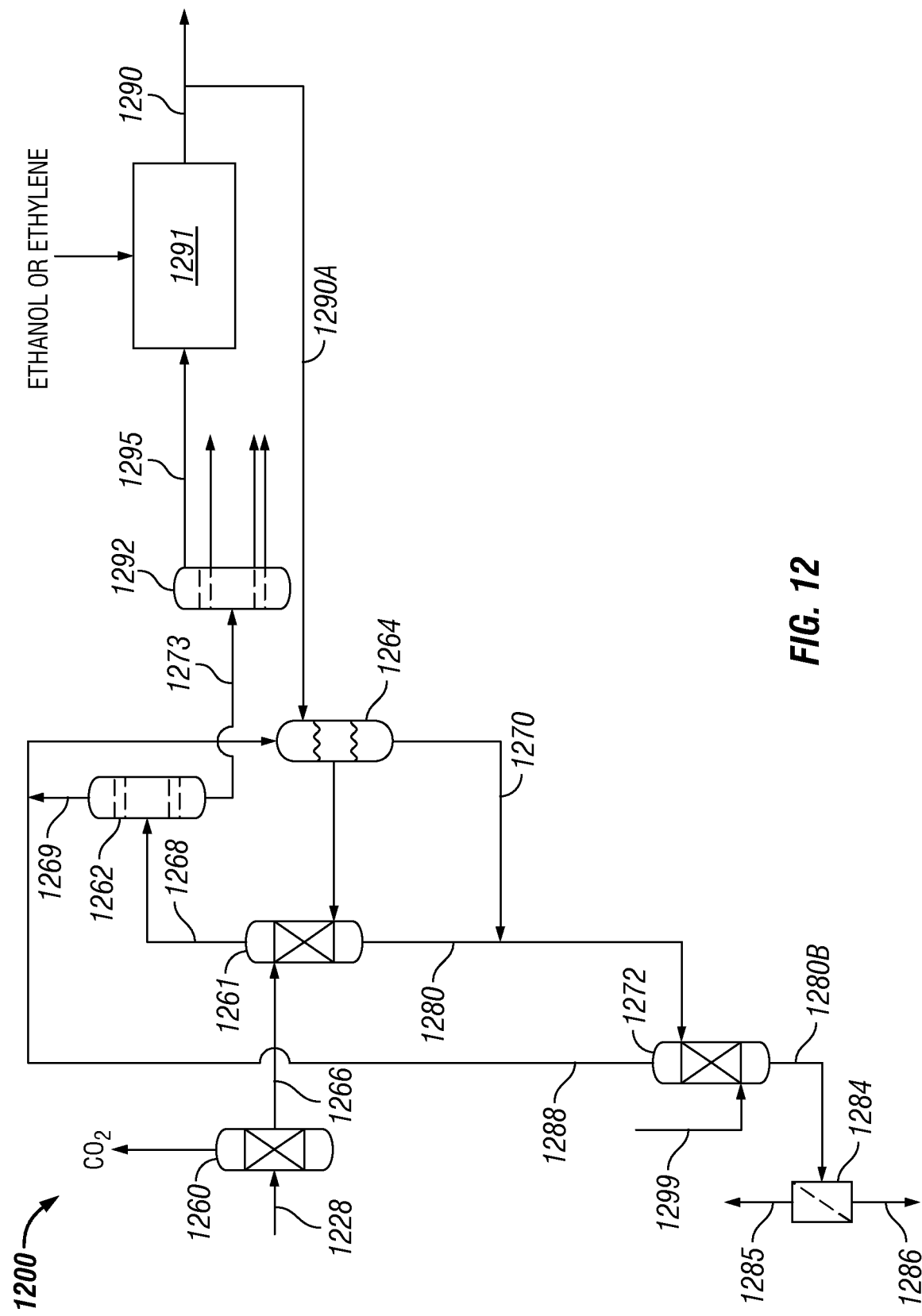
FIG. 12 shows a process that includes integration of carboxylic acid (VFA) extraction with ethyl acetate as the extracting solvent and the conversion of acetic acid into ethyl acetate, according to embodiments of the disclosure.

When using mixed cultures, it is difficult to produce only acetic acid, as higher acids, such as propionic, butyric, valeric, and higher may also be produced. FIG. 12 shows the integration of ethyl acetate liquid-liquid extraction of VFAs from an acidified fermentation broth 1228. Such acidification may take place using the methods, processes, and systems described herein (e.g., FIGS. 2 through 8). The acidified aqueous solution 1228, which may include VFAs, CO2, and ions such as, but not limited to, $Na^+$, $K^+$, $Cl^-$ and $PO4^{3-}$ (i.e., ions that do not tend to form insoluble salts via softening) may be fed to the system 1200. The stream 1228 may undergo gas (e.g., $CO_2$ and other volatile species)

removal by means of, for example, a stripper 1260 or other means known to those skilled in the art.

Any resultant liquid 1266 (which may be substantially or completely $CO_2$-free) may be sent to an Acid Extraction column 1261, where the liquid 1266 may be contacted with a stream 1267 that includes ethyl acetate. The ethyl acetate may extract the VFAs, and the resultant extracted stream 1268 exiting the Acid Extraction unit 1261 may be sent to a Solvent Distillation column 1262 where the ethyl acetate, and in some instances water, may be separated in the distillate from the VFAs, which may exit the bottom of the column. VFAs within bottoms 1273 may go to the Acid Separation Distillation column(s) 1292, where this feed may be separated into acetic acid, propionic acid, butyric acid, and higher acids.

In embodiments, fermentation may be run under conditions that favor acetic acid production, such as higher pH and/or higher temperatures, and there may be very little of the acids higher than C4. Propionic and butyric acids are viable products for export and/or sale, or they may be sent to other conversion processes (e.g., esterification for producing ethyl propionate and ethyl butyrate, respectively).

Acetic acid stream 1295 produced via separation in Acid Separation Distillation column 1292 may be sent to the Ethyl Acetate Production process/system/unit 1291. Such process may be any process known to the skilled in the art for producing ethyl acetate from acetic acid, such as, but not limited to, esterification with ethanol under acidic conditions and gas phase catalytic esterification with ethylene, such as in BP's Avada Process. From the Ethyl Acetate Production process 1291, ethyl acetate stream 1290, which may include pure or substantially pure ethyl acetate, may be obtained as product. At least a portion of ethyl acetate stream 1290 may be recycled (1290A, 1267) back to the Acid Extraction unit 1261 as make-up for any losses of ethyl acetate incurred during the extraction process.

The ethyl acetate stream (which may include some water/steam) that exits as the distillate 1269 from the Solvent Distillation column 1262 may be sent to an organic liquid-aqueous liquid (OLAL) separator 1264, where the water phase and the ethyl acetate phase may be separated in a manner apparent to one of skill in the art. The ethyl acetate phase stream 1267 may be sent to the Acid Extraction unit 1261 for the acid extraction process. The water phase stream 1270 (which may include some ethyl acetate) that exits the OLAL separator 1264 may join the aqueous stream 1280 that exits the Acid Extraction unit 1261.

This aqueous stream may contains ion (e.g., $Na^+$, $K^+$, $Cl^-$, etc) coming from upstream and some ethyl acetate. The above-mentioned joined aqueous streams (i.e., from the OLAL separator and from the Acid Extraction unit) may be sent optionally to a unit 1272, such as, but not limited to, a steam stripper, where the ethyl acetate may be stripped off of the aqueous stream. The ethyl acetate stream 1288 leaving the stripper 1272 may be sent to the OLAL separator 1264 together with the distillate 1269 from the Solvent Distillation column 1262.

Water raffinate 1280B from the steam stripper 1272, which may be lean in VFAs and ethyl acetate and/or contain mostly ions (e.g., $Na^+$, $K^+$, $Cl^-$, etc) coming from upstream, may be sent to an RO system 1284 for concentration and to recover some clean water 1285. At least some of the clean water 1285 may be used in other parts of the process 1200 or other processes, such as the clean water feed to the EAU unit(s) (see FIGS. 2 through 5), or for the regeneration of the cation exchange unit with high-pressure $CO_2$ (see FIGS. 6 and 7), or may be further treated for outfall. The concentrated raffinate 1286 obtained from the RO unit 1284 may be purged from the system as waste, or may be sent upstream to be used as the regenerant for the softener unit(s) (see FIG. 2 through 5).

In some embodiments, the aqueous stream 1280B from the steam stripper unit 1272, prior to and/or after concentration in the RO unit 1284, may be recycled to fermentation, especially if components (e.g., $Na^+$, $Cl^-$, etc) can be purged to avoid or limit accumulation in the process, such as with the fermentation undigested residue, or by purging some of the base produced in the EAU unit (FIGS. 2 through 5), in the regeneration of the ion exchange resin (FIGS. 6 and 7), or in the solvent extraction performed under high-pressure $CO_2$ (FIG. 8).

For the extraction under high-pressure $CO_2$ (FIG. 8), this raffinate stream may be the buffer recycled to the fermentation to control pH after purging a portion of it. Recycling the raffinate to the fermentation may be advantageous because it recycles any unconverted acids, ethyl acetate and the buffer in the case of the process in FIG. 8, thus avoiding or reducing loss.

The esterification of acetic acid with ethanol produces water, which may require separation. For ethyl acetate product, water content may be desired to be low, so more stringent separation may be needed for the ethyl acetate exiting the system; however, the ethyl acetate that is to be recycled to the Acid Extraction unit may include some water, so it may not be necessary to remove all the water from the ethyl acetate recycled as make-up. As such, this ethyl acetate (which may include water) may be sent to the OLAL separator so that the water and ethyl acetate may be separated.

Figure 13A:
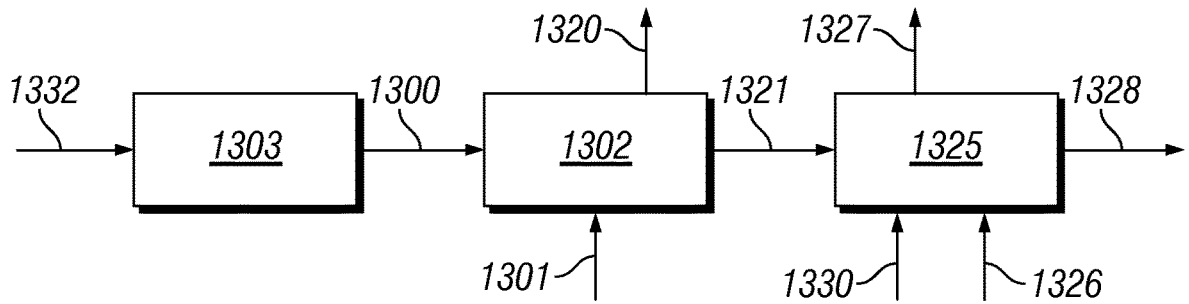
FIGS. 13A-13C show process diagrams that pertain to a fermentation-acidification treatment process and system, according to embodiments of the disclosure.
Figure 13B:
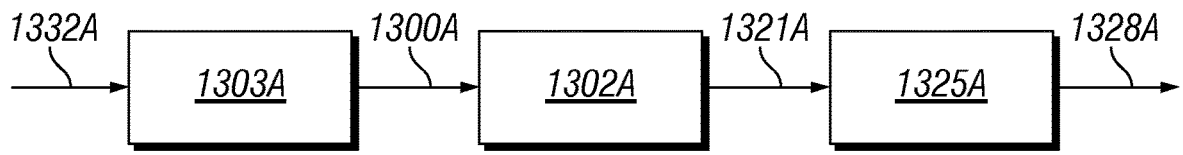

Now with particular reference to FIGS. 13A and 13B together, process diagrams that pertains to a fermentation-acidification-acid product treatment system and process, in accordance with embodiments disclosed herein, is shown. FIGS. 13A and 13B encompasses aspects of process steps, methods, systems, etc. disclosed herein. To that end, FIG. 13A illustrates a system or collection of units for obtaining products from biomass or biomass stream 1332 that may include a fermentation unit or system 1303, an acidification unit or system 1302, and an acidification product treatment unit or system 1325.

In an analogous manner, FIG. 13B also illustrates a process or method that pertains to FIG. 13A with various process steps, including obtaining products from biomass or biomass stream 1332A by way of a fermentation step 1303A, an acidification step 1302A, and an acidification product treatment step 1325A. The system and process may be discussed interchangeably, as one of ordinary skill in the art would understand, for example, that fermentation system 1303 is applicable to a fermentation step 1303A, and vice versa.

With this in mind, fermentation system 1303 may be any vessel or system of vessels of different configurations such as, but not limited to, those described in U.S. patent application Ser. No. 12/708,298, incorporated by reference in its entirety for all purposes, and other peripheral devices such as, but not limited to, grinders, pumps, heat exchangers for keeping the adequate temperature in the fermentation, and liquid/solid separators such as, but not limited to, screw-presses, belt presses, plate-and-frame presses, screens and centrifuges. The fermentation system 1303 may include any unit operation aspects described herein (e.g., FIGS. 2-9), including a screen, clarifier, purifier, concentrator, dewatering, degassifier, softener, etc. (not shown here).

The fermentation broth or product 1300 that exits the fermentation unit 1303, which may contain VFA salts, may be sent to the acidification system 1302 where VFA salts may be converted into acids. The side product stream 1320 may be used in any manner, including recycled to fermentation as described herein. The acidification 1302 may be fed with a utility 1301, which may be water and/or may come from any available sources, such as, but not limited to, from fermentation 1303.

The acidification system 1302 may include various unit operations, such as a degassifier, stripper, etc., which may help remove undesired components, such as gaseous carbon dioxide. Other unit operations include an ion exchange unit(s) (not shown here) as described herein, which may be used to convert these VFA salts to acids. Operation of 1302 may include the use of hydrochloric or sulfuric acid for regeneration purposes.

The acid product stream 1321 may be further treated, such as with RO, prior to being sent to acidification product treatment system 1325. Acid product treatment 1325 may include, for example, acid extraction, where the appropriate solvent 1326 may be used therewith to remove the acids, resulting in byproduct 1327 and followed by the subsequent separation of the acids and the extracting solvent to recover the extracting solvent, which may or may not be recycled within the same acid product treatment operation 1325. Other utilities 1330, such as steam or water, may be used therewith.

The acidification product treatment 1325 may include a number of configurations, including the embodiments or aspects shown in FIGS. 2-9 and aspects of extracting solvent recovery systems where, for example, acids are simply fractionated or the separation of the acids from the ketones or from ethyl acetate as shown in FIGS. 10-12 takes place. Resultant fourth product stream 1328 may be further processed, such as in further acid fractionation or a ketonization or a esterification unit or system (or process), in accordance with embodiments disclosed herein.

Figure 13C:
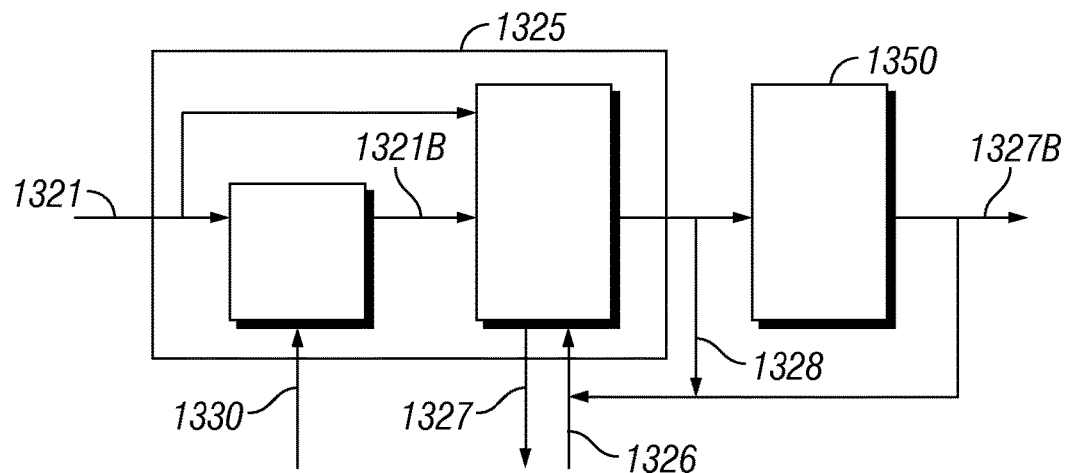

Referring briefly to FIG. 13C, which illustrates an embodiment of the acidification product treatment 1325 and the processing 1350 of the resultant product stream 1328. As shown, the third product stream 1321, or in some instances intermediate third product stream 1321A, may be processed in a manner that includes extraction. As such, acids may be extracted by way of extracting solvent 1326, with subsequent separation of the (used) extracting solvent and acids, resulting in a fourth product stream 1328. The fourth product stream 1328 may be further processed 1350 in accordance with embodiments disclosed herein to produce a fifth product stream 1327B. Fourth product 1328, or at least a portion thereof, or the fifth product stream 1327B, or at least a portion thereof, may be recycled and used as extracting solvent.

Returning now to FIGS. 13A-13B, which illustrate a system or process for producing products from biomass 1332/1332A that may include fermenting 1303/1303A biomass 1332/1332A to produce a first product stream 1300/1300A, which may include carboxylic acid salts. The carboxylic acid salts may include volatile fatty acid (VFA) salts. In aspects, fermentation 1303/1303A may include anaerobic fermentation of biomass 1332/1332A in one or more fermentation vessels. In aspects, the fermentation 1303/1303A may include the production of carbon dioxide from the neutralization with a carbonate buffer of the produced carboxylic acids to form the carboxylic acid salts. In aspects, the fermentation 1303/1303A may include the production of carbon dioxide, methane and hydrogen from the biological conversions in the fermentation. In aspects, the fermentation 1303/1303A may include the elongation of acids into longer chain acids. The longer chain acids may include medium-chain fatty acids (MCFAs). In aspects the MCFAs are carboxylic acids or volatile fatty acids (VFAs) in the range of C4-C11. In aspects, the fermentation 1303/1303A may include the generation of an undigested residue or digestate.

The first product stream 1300/1300A, or a second product stream (not shown), or a combination, may be acidified, such as via acidification 1302/1302A to produce a third product stream 1321/1321A, which may include acids. The second product stream may result from intermediate processing of the first product stream 1300/1300A, and the second product stream may include VFA salts. Intermediate processing of the first product stream 1300/1300A may include at least one of screening, clarifying, dewatering, purifying, concentrating, softening, degasifying, stripping, ion exchange, and combinations thereof, and/or the respective equipment associated therewith. In an embodiment, using ion exchange may include using a cation exchange bed and an anion exchange bed.

The third product stream 1321/1321A may be produced via an EAU unit or system, and may include acids or an acid component(s). Thus, processing of the first and/or second product stream may include acidification by way of EAU. In an embodiment, processing with EAU may result in production of a hydroxide stream, and wherein at least some of the hydroxide stream may be recycled for use in fermentation 1300/1300A. In accordance with embodiments disclosed herein, the EAU may be operably configured with at least 2 stages of electrodialysis via bi-polar membranes (EDBMs). In accordance to other embodiments disclosed herein, the EAU may be operably configured with at least 2 stages of the ABLE system disclosed by Gilliam et al. in U.S. Pat. Nos. 7,993,511, 7,993,500, 7,875,163, 7,790,012, U.S. patent application Ser. No. 12/989,781, U.S. patent application Ser. No. 13/021,355, U.S. patent application Ser. No. 12/952,665 and U.S. patent application Ser. No. 12/991,898 incorporated by reference in their entirety for all purposes.

Processing within acidification 1302/1302A may include acidifying using ion exchange with high pressure $CO_2$ regeneration. Processing within acidification 1302/1302A may include acidifying using high pressure $CO_2$ while performing liquid-liquid extraction.

The third product stream 1321/1321A may be further processed, such as in acidification product treatment 1325/1325A, resulting in a fourth product stream 1328/1328A. Processing of the third product stream 1321/1321A may include using liquid-liquid extraction and further separation of the extracting solvent and the extracted product for extracting solvent recovery. Processing the third product stream 1321/1321A may include at least one of degasifying, deionizing, purifying with reverse osmosis, using liquid-liquid extraction, extracting solvent recovery, and combinations thereof.

In aspects, processing the fourth product stream 1328/1328A may include using a medium-chain fatty acid (MCFA) production process. In aspects, processing the fourth product stream 1328/1328A may include converting at least a portion of the fourth product stream 1328/1328A to ethyl acetate. In aspects, processing the fourth product stream may include reacting at least some of the fourth product stream 1328/1328A to produce ketones. In an embodiment, reacting may occur in a ketone catalytic reactor.

Advantages

Embodiments of the disclosure may provide for operating expenditure savings on dewatering, as a lot of the water does not need to be removed. Embodiments of the disclosure may provide for avoidance of solids handling downstream of the fermentation. Embodiments disclosed herein may provide for very high yields from the ketonization. Beneficially, systems and processes of the disclosure may have one or more reactions occur at lower temperatures. Embodiments may provide for easy recovery of medium-chain fatty acids.

Advantageously, by using the acidification methods described herein, no undesired chemicals need to be added. In addition, as extraction usually represents a large expenditure for solvent losses, usage of the product itself as the extracting solvent, and the integration of the extraction with the production of such solvents makes the process more efficient.

The disclosures of all patents, patent applications, and publications cited herein are hereby incorporated by reference, to the extent they provide some, procedural or other details supplementary to those set forth herein.

EXAMPLES

Example 1

200 mL of a solution containing VFA sodium salts with the acid profile ranging from C2 (acetic) to C8 (octanoic acids) as it would be produced in fermentation (the profile is shown in Table 1), were mixed with 100 mL of octanoic acid under 1000 psi of $CO_2$ pressure at 25° C. The system was allowed to reach equilibrium to allow the acids to be extracted by the octanoic acid and then the aqueous and organic phases were allow to settle and separate without releasing the pressure. A sample of the aqueous phase was taken analyzed using a gas chromatogram (GC) with a flame-ionization detector (FID). The % extraction is shown in Table High extraction efficiency of the acids after undergoing acidification with $CO_2$ is attained, with a trend that shows better extraction for longer acids, especially acids longer than butyric acid. The negative correlation with the extraction of octanoic acid is expected because of the solubility of the octanoic acid extractant in the aqueous phase. Better extraction is expected if several countercurrent stages are implemented as in typical countercurrent liquid-liquid extraction.

Example 2

400 mL of a solution containing VFA sodium salts with the acid profile ranging from C2 (acetic) to C8 (octanoic acids) as it would be produced in fermentation (the profile is shown in Table 2), were mixed with 400 mL of octanoic acid under 500 psi of $CO_2$ pressure at 25° C. The system was allowed to reach equilibrium to allow the acids to be extracted by the octanoic acid and then the aqueous and organic phases were allow to settle and separate without releasing the pressure. A sample of the aqueous phase was taken analyzed using a gas chromatogram (GC) with a flame-ionization detector (FID). The % extraction is shown in Table 2.

TABLE 2

Extraction of VFAs from a sodium VFA salt solution with octanoic acid at 500 psi $CO_2$

|  | Acetic | Propionic | Isobutyric | Butyric | isovaleric | Valeric | Caproic | Heptanoic | Octanoic | Total Acid (g/L) |
|---|---|---|---|---|---|---|---|---|---|---|
| Sodium VFA salt | 5.76 | 3.2 | 0.5 | 5.22 | 0.79 | 2.28 | 4.67 | 1.75 | 0.77 | 24.93 |
| Extraction raffinate | 5.27 | 2.07 | 0.16 | 1.8 | 0.12 | 0.26 | 0.17 | 0.02 | 1.68 | 11.54 |
| extraction % | 8.5% | 35.3% | 68.0% | 65.5% | 84.8% | 88.6% | 96.4% | 98.9% | −118.2% | 53.7% |

Only a small difference in extraction efficiency was attained when the extraction was performed under 500 psi of $CO_2$ pressure compared to 1000 psi of pressure shown in Table 1. Similarly, better extraction efficiency was observed for the higher acids.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or

TABLE 1

Extraction of VFAs from a sodium VFA salt solution with octanoic acid at 1000 psi $CO_2$

|  | Acetic | Propionic | Isobutyric | Butyric | isovaleric | Valeric | Caproic | Heptanoic | Octanoic | Total Acid (g/L) |
|---|---|---|---|---|---|---|---|---|---|---|
| Sodium VFA salts | 5.74 | 3.2 | 0.5 | 5.23 | 0.79 | 2.27 | 4.64 | 1.72 | 0.71 | 24.81 |
| Extraction raffinate | 5.2 | 1.96 | 0.13 | 1.69 | 0.1 | 0.26 | 0.17 | 0.02 | 1.63 | 11.17 |
| Extraction % | 9.4% | 38.8% | 74.0% | 67.7% | 87.3% | 88.5% | 96.3% | 98.8% | −130% | 55.0% | limitations. The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The inclusion or discussion of a reference is not an admission that it is prior art to the present invention, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

What is claimed is:

1. A process for producing short- and medium-chain fatty acids from biomass comprising:
   fermenting biomass to produce a first product stream comprising short- and medium-chain fatty acid salts;
   acidifying at least one of the (a) first product stream, (b) a second product stream derived from intermediate processing of the first product stream, and combinations thereof to produce a third aqueous product stream containing the short- and medium-chain fatty acids;
   separating the short- and medium-chain fatty acids from the third aqueous product stream by liquid-liquid extraction under high pressure carbon dioxide by adding an organic solvent which contains medium-chain fatty acids to form a product stream which comprises short- and medium-chain fatty acids.

2. The process of claim 1, wherein fermenting biomass comprises anaerobic fermentation with a mixed culture of microorganisms in a fermentation vessel or a system of vessels.

3. The process of claim 1, wherein the second product stream results from intermediate processing of the first product stream, and wherein the second product stream comprises volatile fatty acids salts (VFA) or short- and medium-chain fatty acids salts.

4. The process of claim 3, wherein intermediate processing of the first product stream comprises at least one of screening, clarifying, dewatering, purifying, concentrating with membranes, electrodialysis, electrodeionization or evaporators, softening, degasifying, stripping, and ion exchange.

5. The process of claim 1, wherein at least a portion of water in the third aqueous product stream is recycled to the fermentation.

6. The process of claim 1, wherein the medium-chain fatty acids are in the C4-C11 range.

7. The process of claim 1, wherein the medium-chain fatty acids are in the C4-C8 range.

8. A process for producing short- and medium-chain fatty acids from biomass comprising:
   fermenting biomass to produce a first stream comprising medium chain fatty acid salts;
   acidifying the medium-chain fatty acid salts from the first stream to form an aqueous acidified stream containing medium chain fatty acids;
   subjecting the acidified stream to liquid-liquid extraction under high pressure carbon dioxide by adding an organic solvent which contains medium chain fatty acids to form a product stream which comprises medium chain fatty acids.

9. The process of claim 8, wherein the first product stream includes short chain fatty acid salts, wherein short chain fatty acid salts are acidified in the acidifying step and are converted short chain fatty acids, and wherein the product stream includes short chain fatty acids.

10. The process of claim 8, wherein prior to liquid-liquid extraction, the first stream, the aqueous acidified stream, or both the first stream and the aqueous acidified stream are treated (a) to remove solids, (b) to concentrate the short- and medium-chain acid salts, or both, and (c) combinations thereof.

11. The process of claim 10, wherein prior to liquid-liquid extraction, the first stream, the aqueous acidified stream, or both are treated by subjected to screening, clarifying, dewatering, purifying, concentrating with membranes, electrodialysis, electrodeionization or evaporators, softening, degasifying, stripping, ion exchange, or a combination thereof.

12. The process of claim 8, wherein the medium chain fatty acids contain from four to eleven carbons.

13. The process of claim 8, wherein fermenting biomass comprises anaerobic fermentation with a mixed culture of microorganisms in a fermentation vessel or a system of vessels.

* * * * *